(12) United States Patent
Kameshima

(10) Patent No.: US 11,069,637 B2
(45) Date of Patent: Jul. 20, 2021

(54) SEMICONDUCTOR DEVICE, MANUFACTURING METHOD, AND ELECTRONIC DEVICE

(71) Applicant: SONY SEMICONDUCTOR SOLUTIONS CORPORATION, Kanagawa (JP)

(72) Inventor: Takatoshi Kameshima, Kanagawa (JP)

(73) Assignee: SONY SEMICONDUCTOR SOLUTIONS CORPORATION, Kanagawa (JP)

(*) Notice: Subject to any disclaimer, the term of this patent is extended or adjusted under 35 U.S.C. 154(b) by 0 days.

(21) Appl. No.: 16/337,091

(22) PCT Filed: Oct. 5, 2017

(86) PCT No.: PCT/JP2017/036338
§ 371 (c)(1),
(2) Date: Mar. 27, 2019

(87) PCT Pub. No.: WO2018/074250
PCT Pub. Date: Apr. 26, 2018

(65) Prior Publication Data
US 2020/0035630 A1    Jan. 30, 2020

(30) Foreign Application Priority Data
Oct. 19, 2016 (JP) .............................. JP2016-205241

(51) Int. Cl.
| | | |
|---|---|---|
| *H01L 23/00* | (2006.01) | |
| *H01L 23/522* | (2006.01) | |
| *H04N 5/365* | (2011.01) | |
| *H04N 5/374* | (2011.01) | |
| *H01L 23/532* | (2006.01) | |
| *H01L 27/146* | (2006.01) | |

(52) U.S. Cl.
CPC .......... *H01L 24/05* (2013.01); *H01L 23/5226* (2013.01); *H01L 24/03* (2013.01); *H01L 24/08* (2013.01); *H04N 5/365* (2013.01); *H04N 5/374* (2013.01); *H01L 23/53228* (2013.01); *H01L 27/14634* (2013.01); *H01L 2224/0239* (2013.01); *H01L 2224/02372* (2013.01); *H01L 2224/02381* (2013.01); *H01L 2224/05569* (2013.01); *H01L 2224/05647* (2013.01); *H01L 2224/08145* (2013.01)

(58) Field of Classification Search
CPC ......... H01L 27/14603; H01L 27/14636; H01L 27/307; H01L 27/14614; H01L 27/146–14656; H04N 5/379
USPC ................ 257/225–234, 257, 258, 291–294, 257/431–448
See application file for complete search history.

(56) References Cited

U.S. PATENT DOCUMENTS

| | | | |
|---|---|---|---|
| 2004/0137701 A1* | 7/2004 | Takao ................ | H01L 23/3114 438/461 |
| 2010/0096760 A1 | 4/2010 | Yu et al. | |
| 2010/0155796 A1* | 6/2010 | Koike ................. | H01L 23/481 257/292 |
| 2015/0054110 A1 | 2/2015 | Kashihara | |
| 2019/0115387 A1* | 4/2019 | Yamagishi ....... | H01L 27/14636 |

FOREIGN PATENT DOCUMENTS

| | | |
|---|---|---|
| CN | 101728371 A | 6/2010 |
| CN | 104425531 A | 3/2015 |
| JP | 2005-135988 A | 5/2005 |
| JP | 2010-021489 A | 1/2010 |
| JP | 2010-103533 A | 5/2010 |
| JP | 2015-041677 A | 3/2015 |
| JP | 2016-181531 A | 10/2016 |
| KR | 10-2010-0044100 A | 4/2010 |
| TW | 201017847 A | 5/2010 |
| WO | 2016/152513 A1 | 9/2016 |

OTHER PUBLICATIONS

International Search Report and Written Opinion of PCT Application No. PCT/JP2017/036338, dated Dec. 5, 2017, 9 pages of ISRWO.

* cited by examiner

*Primary Examiner* — Xi Wang
(74) *Attorney, Agent, or Firm* — Chip Law Group

(57) ABSTRACT

Provided is a semiconductor device, a manufacturing method, and an electronic device designed to suppress the occurrence of Cu pumping. The semiconductor device includes a Cu electrode pad serving as a bonding surface for bonding a plurality of semiconductor members together and an electrode via, the electrode via being a connection member that connects the Cu electrode pad to a lower-layer metal. The Cu electrode pad is formed in a location displaced from the electrode via.

9 Claims, 24 Drawing Sheets

SEMICONDUCTOR DEVICE, MANUFACTURING METHOD, AND ELECTRONIC DEVICE

CROSS REFERENCE TO RELATED APPLICATIONS

This application is a U.S. National Phase of International Patent Application No. PCT/JP2017/036338 filed on Oct. 5, 2017, which claims priority benefit of Japanese Patent Application No. JP 2016-205241 filed in the Japan Patent Office on Oct. 19, 2016. Each of the above-referenced applications is hereby incorporated herein by reference in its entirety.

TECHNICAL FIELD

The present disclosure relates to a semiconductor device, a manufacturing method, and an electronic device and, in particular, relates to a semiconductor device, a manufacturing method, and an electronic device designed to suppress the occurrence of Cu pumping.

BACKGROUND ART

To fabricate a semiconductor device including a three-dimensional integrated circuit and the like, a method is sometimes used in which Cu electrodes provided in the bonding surfaces of semiconductor members are directly bonded together.

For example, Patent Literature 1 discloses that a first substrate in which a light receiving element is formed is bonded, by using Cu electrode pads (bonding pads), to a second substrate in which a peripheral circuit is formed. In such a method, in each of the semiconductor members, a Cu electrode and an interlayer insulating film are provided in the same plane to serve as a bonding surface and are then planarized, and joining is performed to bond the opposing Cu electrodes together and the opposing interlayer insulating films together.

To fabricate a more robust three-dimensional integrated circuit or the like, it is required that a stronger bond be achieved. Patent Literature 2 discloses a technique for achieving a stronger bond. In the technique, a specific proportion of dummy Cu electrodes are provided in the bonding surface to suppress the occurrence of dishing, erosion, and the like attributable to chemical mechanical polishing (CMP) in the bonding surfaces of the semiconductor members, thereby achieving high planarity.

Furthermore, Patent Literature 2 also discloses a technique in which the dummy Cu electrodes provided to suppress dishing are also directly bonded together to increase the proportion of Cu solid phase diffusion connection in the bonding of semiconductor members, thereby achieving a strong bond. In Patent Literature 2, it is also disclosed that the proportion of Cu electrodes and the dummy Cu electrodes in the bonding surface is optimally 50 to 60%.

As described above, in Patent Literature 1 and Patent Literature 2, a stronger bond is achieved in such a manner that semiconductor members each having a highly planar bonding surface in which Cu electrodes and dummy Cu electrodes are provided in a proportion of 50 to 60% are tentatively bonded together in a room-temperature environment and are thereafter subjected to a heat treatment in a high-temperature environment at 350° C.

CITATION LIST

Patent Literature

Patent Literature 1: JP 2006-191081A
Patent Literature 2: JP 2012-256736A

DISCLOSURE OF INVENTION

Technical Problem

However, Cu has a characteristic of undergoing variations in volume in accordance with the coefficient of thermal expansion, and therefore, when the volume of Cu electrodes and Cu dummy electrodes is large, Cu pumping tends to occur because the volume increases in accordance with the coefficient of thermal expansion.

In addition, in a structure as disclosed in Patent Literature 2, the Cu volume of the Cu electrode, which is connected to the lower-layer metal, is larger than the Cu volume of the dummy Cu electrode, and therefore the structure is more susceptible to the occurrence of Cu pumping.

The present disclosure has been made in view of such circumstances and makes it possible to suppress the occurrence of Cu pumping.

Solution to Problem

A semiconductor device according to an aspect of the present technology includes: a Cu electrode pad serving as a bonding surface for bonding a plurality of semiconductor members together; and an electrode via, the electrode via being a connection member that connects the Cu electrode pad to a lower-layer metal. The Cu electrode pad is formed in a location displaced from the electrode via.

The electrode via can serve as a vertical signal line.
The electrode via can include Cu.
The Cu in the electrode via can have a volume of $1.0E+10$ $nm^3$ or greater.
An electrically conductive metal that connects the electrode via to the Cu electrode pad can be further included. The electrically conductive metal can be structured to cover a top of the electrode via.
The electrically conductive metal can be aluminum or tungsten.
A Cu interconnect that connects the electrode via to the Cu electrode pad can be further included.
The electrode via can be structured such that an electrically conductive metal other than Cu is formed on a side wall to be able to electrically connect at least the electrode via and the Cu electrode pad together and a space inside the side wall is filled with an insulating film.
The electrode via can be structured such that the electrically conductive metal is formed to cover the side wall and the space inside the side wall is filled with the insulating film.
In accordance with volumes of the semiconductor members, the Cu electrode pad and the electrode via can be provided in each of the semiconductor members to be bonded together.
The Cu electrode pad and the electrode via can be provided in one of the semiconductor members to be bonded together, and a Cu electrode can be provided in another of the semiconductor members, the Cu electrode including the Cu electrode pad and a Cu electrode via formed immediately below the Cu electrode pad.

The semiconductor device can be a solid-state imaging device.

A manufacturing method according to an aspect of the present technology includes, by a manufacturing apparatus: forming an electrode via, the electrode via being a connection member that connects a Cu electrode pad to a lower-layer metal, the Cu electrode pad serving as a bonding surface for bonding a plurality of semiconductor members together; and forming the Cu electrode pad in a location displaced from the electrode via.

An electronic device according to an aspect of the present technology includes: a solid-state imaging device including a Cu electrode pad serving as a bonding surface for bonding a plurality of semiconductor members together, and an electrode via, the electrode via being a connection member that connects the Cu electrode pad to a lower-layer metal, the Cu electrode pad being formed in a location displaced from the electrode via; a signal processing circuit configured to process an output signal output from the solid-state imaging device; and an optical system through which incident light passes to enter the solid-state imaging device.

In an aspect of the present technology, an electrode via is formed, the electrode via being a connection member that connects a Cu electrode pad to a lower-layer metal, the Cu electrode pad serving as a bonding surface for bonding a plurality of semiconductor members together. Then, the Cu electrode pad is formed in a location displaced from the electrode via.

Advantageous Effects of Invention

With the present technology, semiconductor members can be bonded together. In particular, with the present technology, the occurrence of Cu pumping can be suppressed.

The advantageous effects described in the present specification are merely exemplary and the advantageous effects of the present technology are not limited to the advantageous effects described in the present specification, but there may be additional advantageous effects.

MODE(S) FOR CARRYING OUT THE INVENTION

Figure 1:
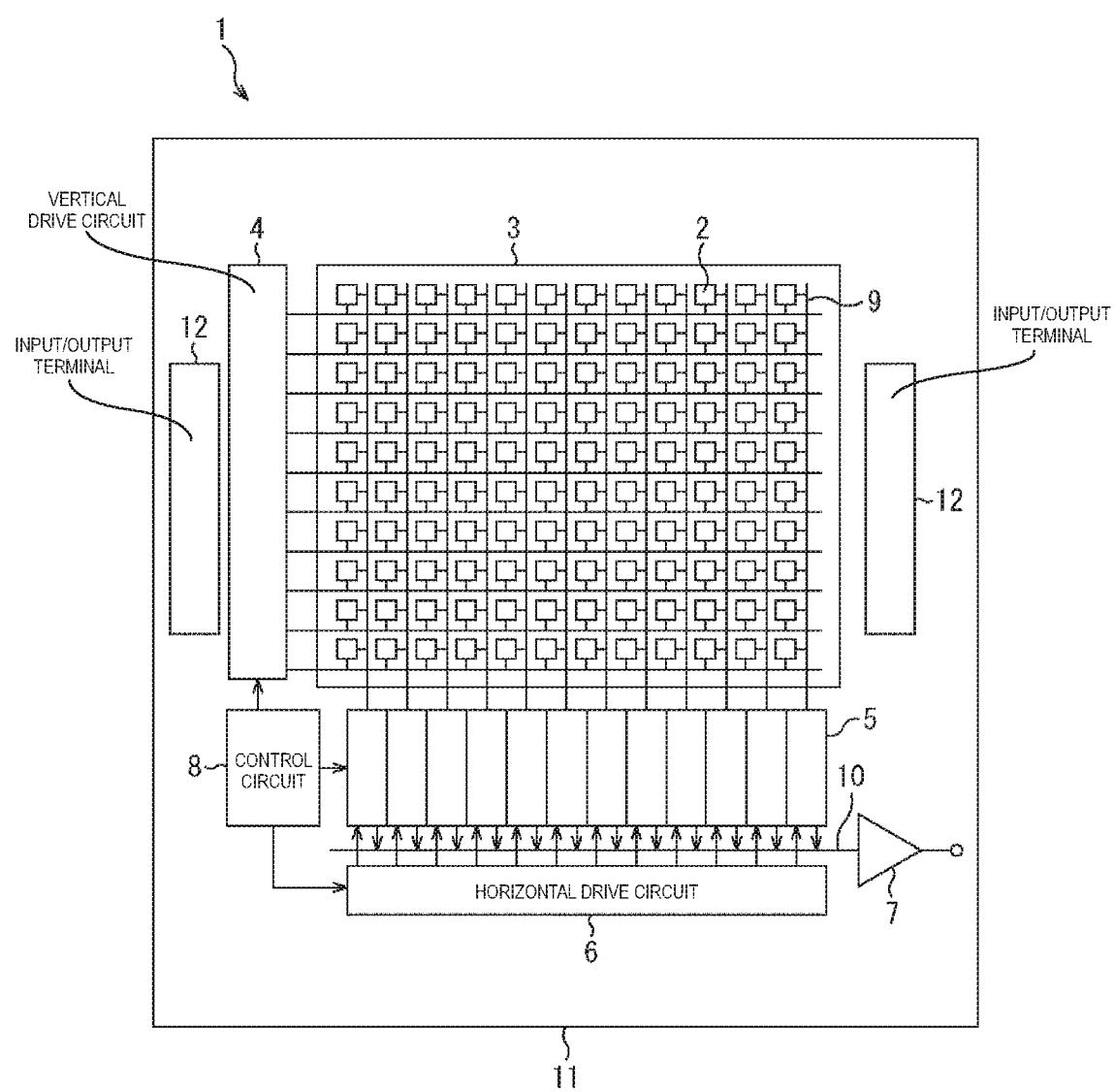
FIG. 1 is a block diagram illustrating a schematic configuration example of a solid-state imaging device employing the present technology.

Modes for carrying out the present disclosure (hereinafter referred to as embodiments) will now be described. Note that the descriptions will be given in the following order.
0. Configuration of device
1. First Embodiment
2. Second Embodiment
3. Third Embodiment
4. Fourth Embodiment
5. Usage examples of image sensor
6. Example of electronic device
7. Application example to endoscopic surgery system
8. Application example to mobile body

0. Configuration of Device

<Schematic Configuration Example of Solid-State Imaging Device>

FIG. 1 illustrates a schematic configuration example of an example of a complementary metal oxide semiconductor (CMOS) solid-state imaging device that is applied to each of the embodiments of the present technology.

As illustrated in FIG. 1, a solid-state imaging device (device chip) 1 includes a semiconductor substrate 11 (e.g., silicon substrate), which includes a pixel region (so-called imaging region) 3 and a peripheral circuit region. In the pixel region 3, a plurality of pixels 2, each of which includes a photoelectric conversion element, are two-dimensionally arranged in a regular manner.

The pixel 2 includes a photoelectric conversion element (e.g., photo diode (PD)) and a plurality of pixel transistors (so-called MOS transistors). The plurality of pixel transistors may include three transistors, which are, for example, a transfer transistor, a reset transistor, and an amplifying transistor or may include four transistors, with the addition of a selection transistor.

Furthermore, the pixel 2 may be a pixel sharing structure. The pixel sharing structure includes a plurality of photodiodes, a plurality of transfer transistors, a shared floating diffusion, and the remaining pixel transistors, each of which is provided singularly and shared. The photodiode is a photoelectric conversion element.

The peripheral circuit region includes a vertical drive circuit 4, a column signal processing circuits 5, a horizontal drive circuit 6, an output circuit 7, and a control circuit 8.

The control circuit 8 receives an input clock and data for commanding an operation mode and the like and outputs data such as internal information of the solid-state imaging device 1. Specifically, on the basis of a vertical synchronization signal, a horizontal synchronization signal, and a master clock, the control circuit 8 generates a clock signal and a control signal that serve as the basis for the operations of the vertical drive circuit 4, the column signal processing circuits 5, and the horizontal drive circuit 6. Subsequently, the control circuit 8 inputs these signals to the vertical drive circuit 4, the column signal processing circuits 5, and the horizontal drive circuit 6.

The vertical drive circuit 4 includes, for example, a shift register. The vertical drive circuit 4 selects a pixel drive interconnect and supplies a pulse for driving the pixel 2 to the selected pixel drive interconnect to drive the pixels 2 on a row-by-row basis. Specifically, the vertical drive circuit 4 performs selective scanning of the individual pixels 2 of the pixel region 3 on a row-by-row basis sequentially in the vertical direction and supplies a pixel signal based on a signal charge generated in accordance with the amount of received light in the photoelectric conversion element of each of the pixels 2 to the column signal processing circuits 5 through vertical signal lines 9.

The column signal processing circuit 5 is disposed, for example, for each of the columns of the pixels 2 and performs, on a per pixel row basis, signal processing such as noise removal on signals output from the corresponding row of pixels 2. Specifically, the column signal processing circuit 5 performs signal processing, such as correlated double sampling (CDS) for removing fixed pattern noise specific to the pixel 2, signal amplification, and AD (analog-to-digital) conversion. A horizontal selection switch (not illustrated) is provided at the output stage of the column signal processing circuits 5 and is connected to the horizontal signal line 10.

The horizontal drive circuit 6 includes, for example, a shift register. The horizontal drive circuit 6 sequentially outputs a horizontal scanning pulse to thereby select each of the column signal processing circuits 5 in turn and causes the pixel signal to be output from each of the column signal processing circuits 5 to the horizontal signal line 10.

The output circuit 7 performs signal processing on the signal sequentially supplied from each of the column signal processing circuits 5 through the horizontal signal line 10 and outputs the signal. For example, the output circuit 7 performs, in some cases, only buffering and, in other cases, performs black level adjustment, column variation correction, various kinds of digital signal processing, and the like.

Input/output terminals 12 are provided to exchange signals with external devices.

1. First Embodiment

<Configuration Example of Manufacturing Apparatus>

Figure 2:
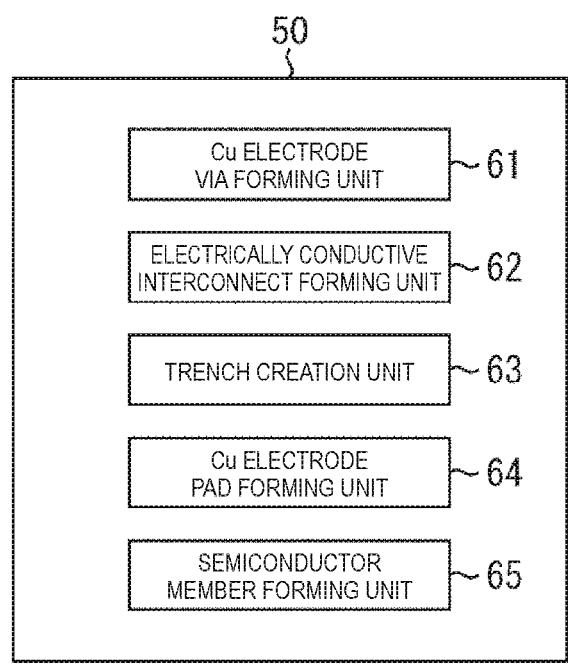
FIG. 2 is a block diagram illustrating a configuration example of a manufacturing apparatus for manufacturing a semiconductor device, which is a solid-state imaging element, of a first embodiment of the present technology.

FIG. 2 is a block diagram illustrating a configuration example of a manufacturing apparatus for manufacturing a semiconductor device, which is a solid-state imaging device, of the first embodiment of the present technology.

With the manufacturing apparatus of FIG. 2, in the fabrication of the Cu electrode used for bonding in the semiconductor device that is a solid-state imaging device of the first embodiment of the present technology, a Cu electrode pad and a Cu electrode via, which are among Cu electrode members, are formed to be displaced relative to each other, that is, to be distant from each other. The Cu electrode pad is a member to which planarization is applied and where connection (bonding) is performed, and the Cu electrode via is a member used for contact with a lower-layer metal.

In the example of FIG. 2, a manufacturing apparatus 50 includes a Cu electrode via forming unit 61, an electrically conductive interconnect forming unit 62, a trench creation unit 63, a Cu electrode pad forming unit 64, and a semiconductor member forming unit 65.

The Cu electrode via forming unit 61 forms the Cu electrode via. The electrically conductive interconnect forming unit 62 forms an electrically conductive interconnect for conductively connecting the Cu electrode pad to the Cu electrode via. The trench creation unit 63 creates a trench portion for forming the Cu electrode pad.

The Cu electrode pad forming unit 64 forms the Cu electrode pad. The semiconductor member forming unit 65 forms a semiconductor device by bonding semiconductor members together.

<Operation Example of Manufacturing Apparatus>

Figure 3:
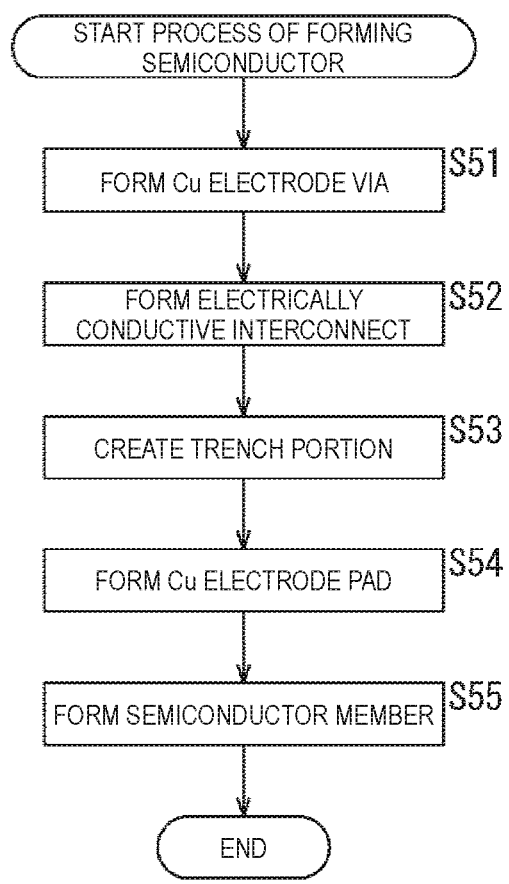
FIG. 3 is a flowchart illustrating a process of forming a semiconductor performed by the manufacturing apparatus of FIG. 2.

The following description describes, with reference to the flowchart of FIG. 3, a process of forming the semiconductor that is a solid-state imaging element of the first embodiment of the present technology. Note that the process of forming the semiconductor of FIG. 3 will be described by referring to the process diagrams of FIGS. 4A, 4B, 4C, and 5 where appropriate. Furthermore, in the process diagrams of FIGS. 4A, 4B, and 4C and subsequent drawings, the bold line represents a barrier metal.

Figure 4A:
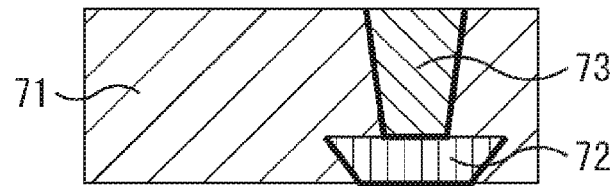
FIGS. 4A, 4B, and 4C are process diagrams illustrating the process of forming a semiconductor of FIG. 3.

In step S51, as illustrated in FIG. 4A, the Cu electrode via forming unit 61 forms a Cu electrode via 73 in an insulating film 71 over a Cu electrode via contact metal 72. That is, the Cu electrode via contact metal 72 is first formed, and the insulating film 71 is formed thereover. A Cu electrode via hole is formed on the Cu electrode via contact metal 72 in the insulating film 71, thereby forming the Cu electrode via 73. During that time, the Cu electrode via 73 is formed by forming a Cu interconnect and thereafter performing, on the Cu interconnect, a lithography process, a dry etching process, a sputtering process, a Cu plating process, and a CMP process, in accordance with the back end of line (BEOL) process.

Figure 4B:
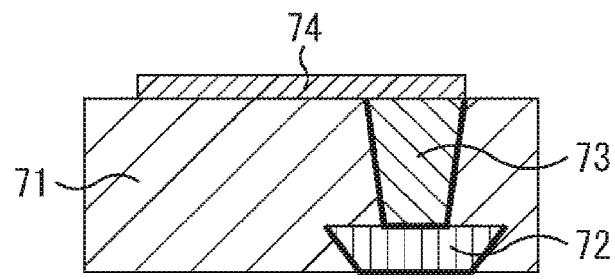

Next, in step S52, as illustrated in FIG. 4B, the electrically conductive interconnect forming unit 62 forms an electrically conductive interconnect 74, which conductively connects the Cu electrode via 73 to the Cu electrode pad, which is formed to be displaced. The electrically conductive interconnect 74 is formed by forming a film of a metal, such as aluminum (Al) or tungsten (W), and thereafter performing a lithography process and a dry etching process, in such a manner as to cover the Cu electrode via 73. Note that the electrically conductive interconnect 74 may be formed by using Cu by creating a shallow damascene.

The width of the electrically conductive interconnect 74 is set in accordance with the size of the Cu electrode pad. For this, setting to a width greater than the size of the Cu electrode pad ensures a margin, which makes it possible to form a robust Cu electrode.

Figure 4C:
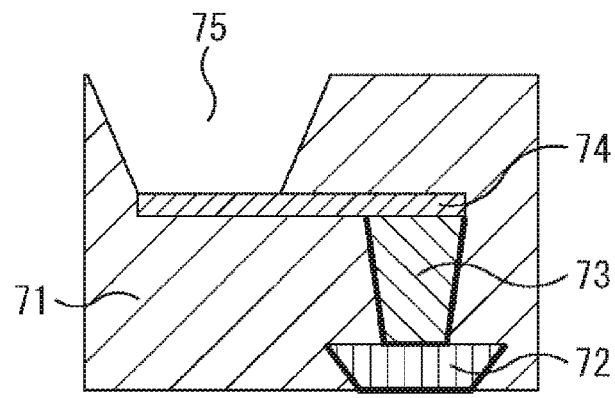

In step S53, as illustrated in FIG. 4C, the trench creation unit 63 creates, in a location away from the Cu electrode via 73, a trench portion 75 for forming the Cu electrode pad.

Here, it is necessary that the displacement width between the Cu electrode via 73 and the Cu electrode pad be set such that there is no overlap between the Cu electrode via 73 and the Cu electrode pad. If there is an overlapping portion of the Cu electrode via 73 and the Cu electrode pad, Cu volume thermal expansion stress of the Cu electrode via 73 is transmitted to the Cu electrode pad, and pumping occurs, which degrades bonding characteristics and reliability.

That is, if Cu pumping occurs in one or more of the Cu electrodes at the bonding interface, the bonding surfaces partially separate from each other because of the Cu electrode experiencing the occurrence of Cu pumping, and as a result, a void is formed. If a void occurs, the bonding interface strength of a semiconductor device including, for example, a three-dimensional integrated circuit decreases.

Furthermore, in Cu electrodes not having the occurrence of pumping, a connection (conductive connection) failure occurs due to separation between opposing electrodes. In addition, because of a void between the insulating films, short circuiting between adjacent Cu electrodes or degradation of element reliability, particularly time dependent dielectric breakdown (TDDB) occurs, and, depending on the conditions, the semiconductor device cannot be put on the market.

To address this, a displacement of a minimum width of 1 pitch (size of Cu electrode) may be made in the case where the design layout is such that the sizes and the arrangement pitches of the Cu electrode pads and the dummy Cu electrode pads are uniform. As a result, the Cu electrode pads are free from the influence of Cu volume thermal expansion stress of the Cu electrode vias 73.

Figure 5:
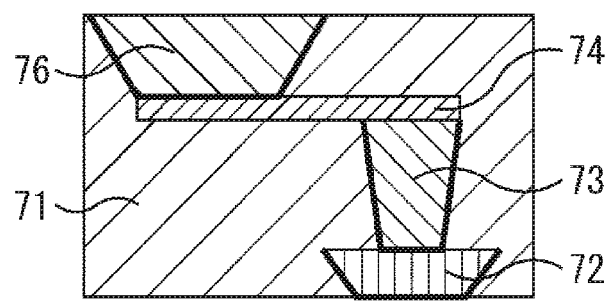
FIG. 5 is a process diagram illustrating the process of forming a semiconductor of FIG. 3.

Next, in step S54, as illustrated in FIG. 5, the Cu electrode pad forming unit 64 fills the trench portion 75 with Cu by performing a sputtering process and a Cu plating process and then performs a CMP process to form a Cu electrode pad 76, which is sufficiently planar to serve as a bonding surface.

Figure 6:
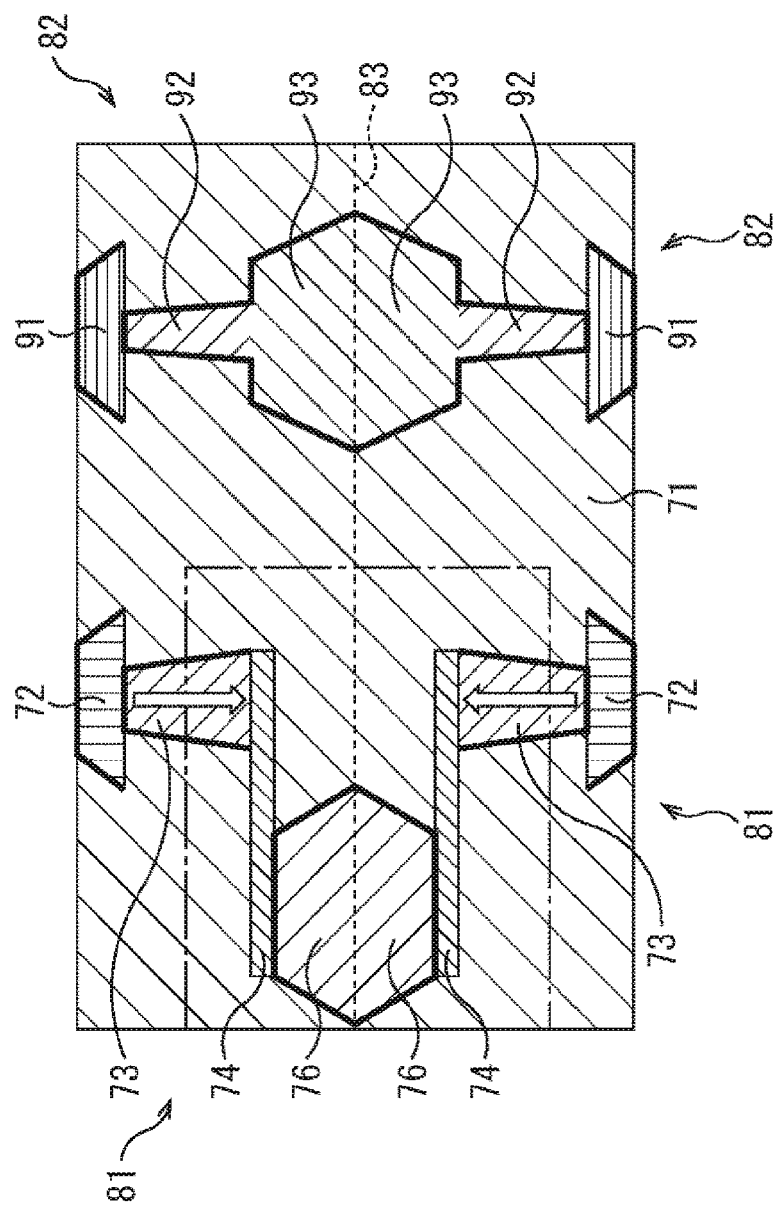
FIG. 6 is a diagram illustrating an example of a semiconductor device formed by joining two semiconductor members together at their bonding surfaces.

In step S55, the semiconductor member forming unit 65 forms a semiconductor device as illustrated in FIG. 6 by bonding together semiconductor members in each of which is formed a displaced Cu electrode member 81, which has a structure including the Cu electrode via contact metal 72, the Cu electrode via 73, the electrically conductive interconnect 74, and the Cu electrode pad 76.

The example of FIG. 6 represents a semiconductor device including two semiconductor members joined together at bonding surfaces 83. In this semiconductor device, a Cu electrode structure in which displaced Cu electrode members 81 are bonded together and a Cu electrode structure in which non-displaced Cu electrode members 82 are bonded together coexist in the insulating film 71.

The displaced Cu electrode member 81 includes the Cu electrode via contact metal 72, the Cu electrode via 73, the electrically conductive interconnect 74, and the Cu electrode pad 76. On the other hand, the non-displaced Cu electrode member 82 includes a Cu electrode via contact metal 91, a Cu electrode via 92, which is smaller in volume than the Cu electrode via 73, and a Cu electrode pad 93.

That is, in the exemplary semiconductor device of FIG. 6, the Cu electrode via 92, which has a different volume than the Cu electrode via 73, coexists, but good bonding characteristics are achieved even though Cu electrode vias of different volumes coexist.

The reason for this is as follows. The influence of Cu volume thermal expansion stress is doubly prevented, that is, the influence of Cu volume thermal expansion stress is prevented by the structure in which the Cu electrode pad 76 is displaced relative to the Cu electrode via 73, and in addition, the Cu electrode via 73 is capped with the electrically conductive interconnect 74, which connects the Cu electrode via 73 to the Cu electrode pad 76. As a result, pumping is suppressed, and therefore better bonding characteristics and high reliability are achieved.

Furthermore, in the case where the Cu electrode via 73 is a through silicon via (TSV), the risk of the occurrence of Cu pumping is accelerated because volume thermal expansion stress applied has a vector (indicated by arrow in drawings) and the stress is concentrated in the Cu electrode pad 76, in which the expansion is not interfered with, but countermeasures can be taken by virtue of the structure described above with reference to FIG. 5, which includes the Cu electrode via contact metal 72, the Cu electrode via 73, the electrically conductive interconnect 74, and the Cu electrode pad 76.

Here, in the case where the Cu electrode via 73 is a TSV, the Cu volume is not less than $1.0E+10$ $nm^3$ because, for example, the via diameter is not less than 3000 nm in diameter and the via height is not less than 6000 nm, in contrast to mass-produced Cu electrode vias 73. The value of the Cu volume is two or more orders of magnitude larger than those of mass-produced Cu electrode vias, and therefore the risk of the occurrence of Cu pumping increases. Accordingly, in the case where the Cu volume of the Cu electrode via 73 is not less than $1.0E+10$ $nm^3$, the Cu electrode structure of the displaced Cu electrode member 81, which includes the Cu electrode via contact metal 72, the Cu electrode via 73, the electrically conductive interconnect 74, and the Cu electrode pad 76, is a more effective countermeasure.

Figure 7:
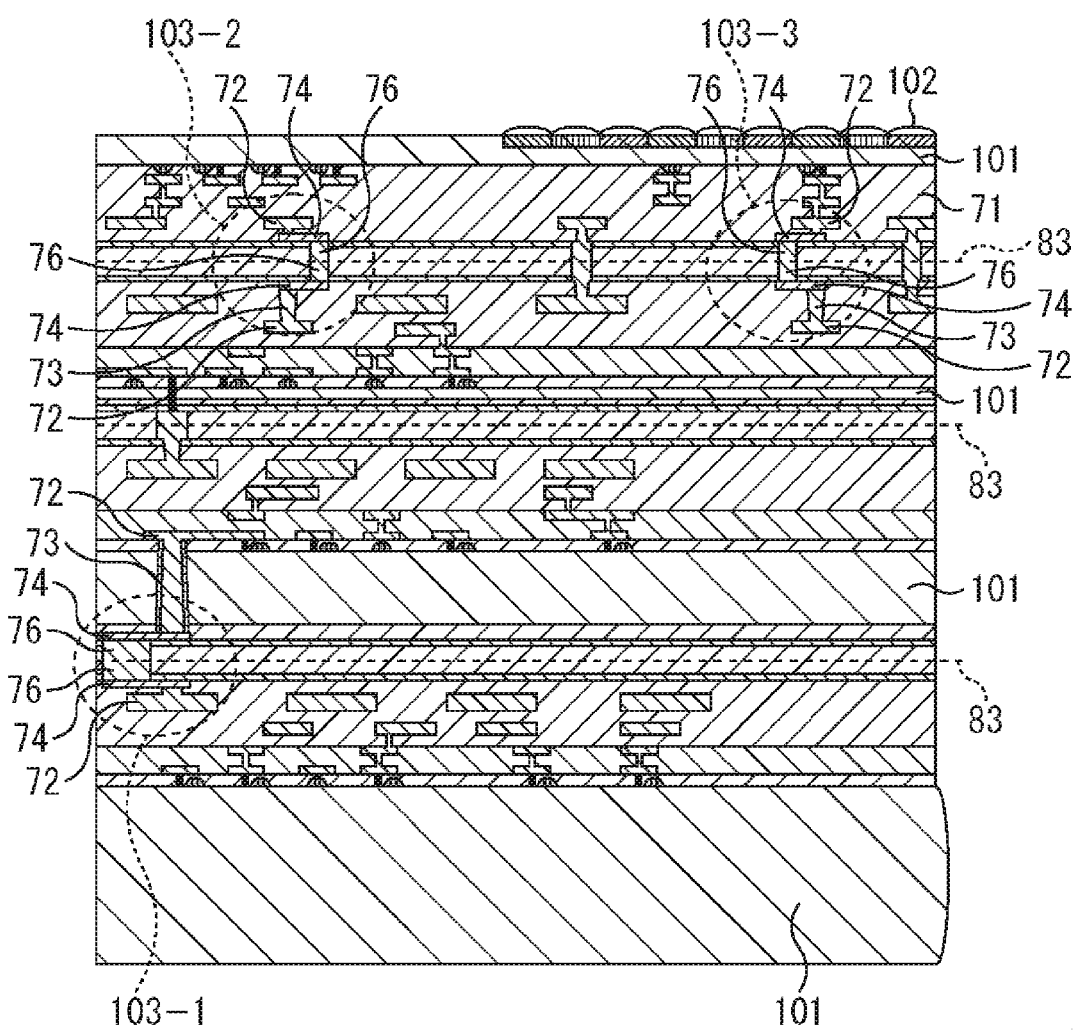
FIG. 7 is a diagram illustrating an example of a semiconductor device formed by joining a plurality of semiconductor members together at their bonding surfaces.

FIG. 7 illustrates an example of a structure of a solid-state imaging device in which three or more semiconductor members each including a Si substrate 101 are stacked by being bonded together at the bonding surfaces 83 and in which a TSV is provided as a vertical signal line for photoelectric conversion. Note that lenses and color filters 102 are formed on the uppermost layer.

In the case where the TSV is a Cu electrode via and is connected to a Cu electrode pad, the direction of Cu volume thermal expansion (stress) is concentrated in the Cu electrode pad, which has lower resistance than in the lateral direction, in which the TSV is sandwiched by the Si substrate, and as a result, the risk increases. In addition, since a barrier metal (BM) exists between the Cu electrode via and a lower-layer metal, stress is concentrated in the Cu electrode pad, which is in an upper layer over the Cu electrode via, and as a result, the risk increases.

In view of this, structures 103-1 to 103-3, in which displaced Cu electrode members are bonded together, as referenced in FIG. 6, are employed for Cu electrodes that have the risk of the occurrence of pumping, and, for example, in the structure 103-1, in which displaced Cu electrode members are bonded together, the use of the Cu electrode via 73 as the TSV suppresses pumping.

In the example of FIG. 7, too, dummy Cu electrodes as described in Patent Literature 2 are also disposed although not explicitly illustrated. Here, with regard to the amount of displacement, it is necessary that the displacement ensure that the Cu electrode pads and the dummy Cu electrode pads are not disposed immediately over the Cu electrode vias and that the Cu electrode vias and the Cu electrode pads (including dummies) are not in contact with each other.

For example, in the case where Cu electrodes and dummy Cu electrodes are both disposed at a uniform pitch, making a displacement of ½ pitch makes it possible to obtain a design in which the space between adjacent Cu electrodes is positioned immediately over the Cu electrode via.

Note that the Cu electrode via is used as a vertical signal line in the periphery of the pixel region, but, in the pixel region, the Cu electrode via is used not only as a vertical signal line but also for blocking light, for example.

Figure 8:
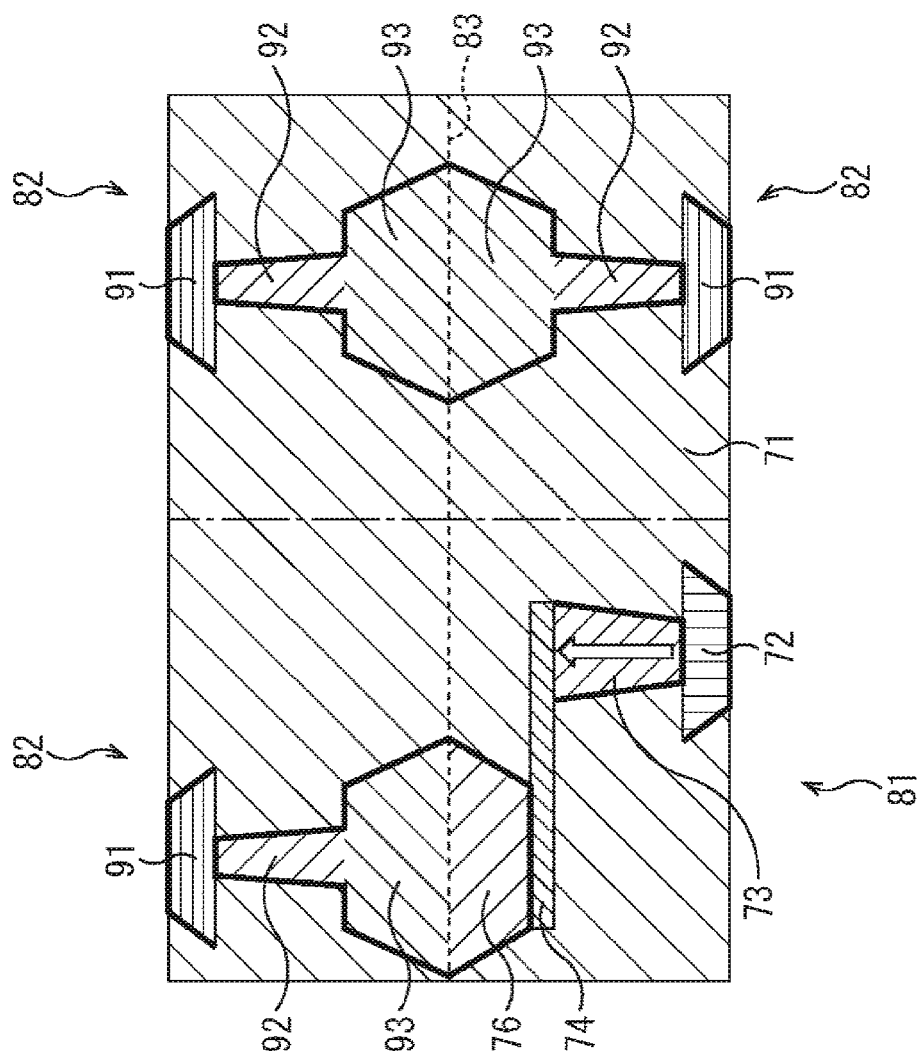
FIG. 8 is a diagram illustrating an example of a semiconductor device formed by joining two semiconductor members together at their bonding surfaces.

Here, FIG. 6 and FIG. 7 illustrate a Cu electrode structure in which the displaced Cu electrode members 81 are bonded together in the fabrication of Cu electrodes that are used for bonding in a semiconductor device; however, in the case where the volume of each of the Cu electrode vias of one semiconductor member is less than $1.0E+10$ nm$^3$ and there is no risk of the occurrence of pumping, it is also possible to fabricate a semiconductor device by employing a Cu electrode structure in which a non-displaced Cu electrode member 82 and a displaced Cu electrode member 81 are bonded together, as illustrated in FIG. 8.

In this manner, an appropriate process (Cu electrode) can be selected in accordance with the conditions of the Cu electrodes, thereby reducing the cost.

Figure 9:
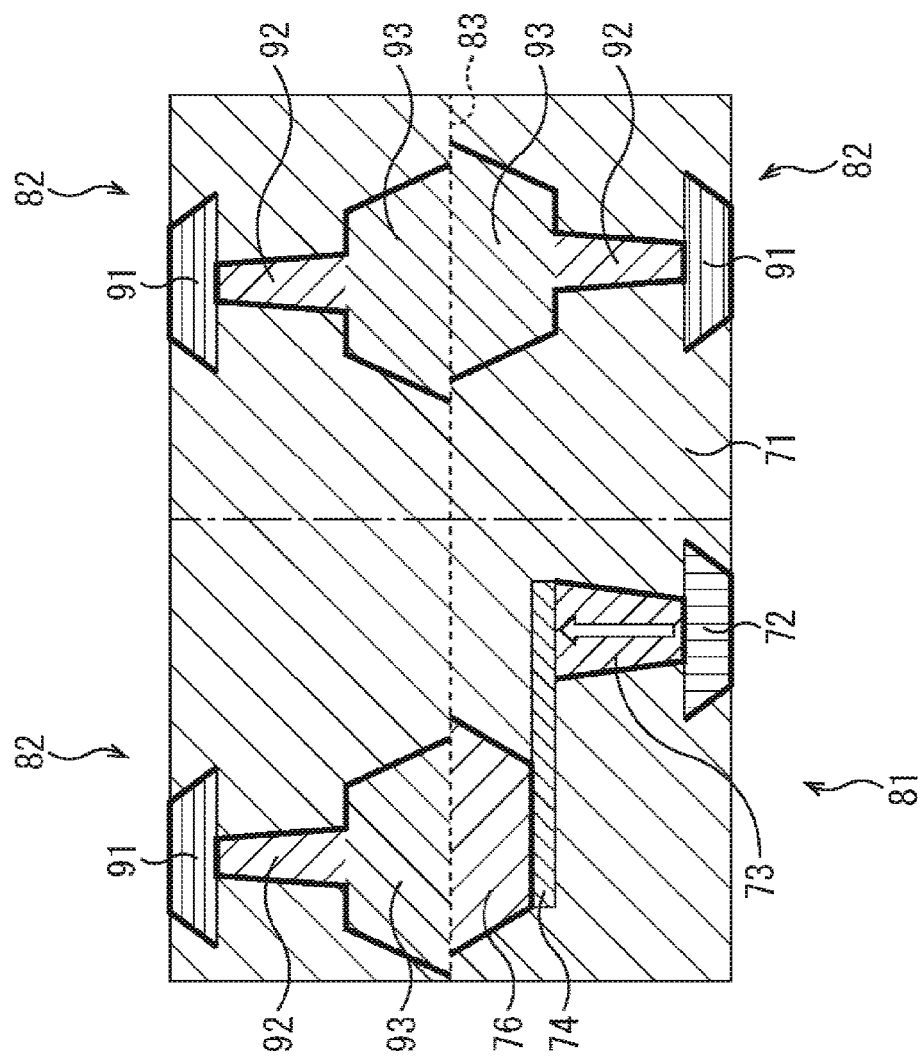
FIG. 9 is a diagram illustrating another example of a semiconductor device formed by joining two semiconductor members together at their bonding surfaces.

Note that, as illustrated in FIG. 9, at the bonding surfaces 83, the Cu electrode pads to be bonded together may be slightly displaced relative to each other in the left and right direction (in FIG. 9, right direction as viewed) provided that the Cu electrode pads are electrically connected to each other.

2. Second Embodiment

<Configuration Example of Manufacturing Apparatus>

Figure 10:
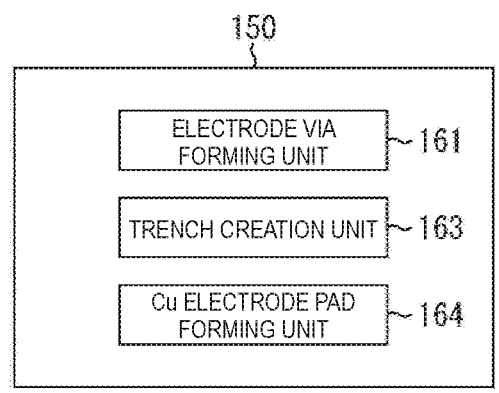
FIG. 10 is a block diagram illustrating a configuration example of a manufacturing apparatus for manufacturing a semiconductor device, which is a solid-state imaging element, of a second embodiment of the present technology.

FIG. 10 is a block diagram illustrating a configuration example of a manufacturing apparatus for manufacturing a semiconductor device, which is a solid-state imaging device, of the second embodiment of the present technology.

With the manufacturing apparatus of FIG. 10, too, in the fabrication of the Cu electrode used for bonding in the semiconductor device that is a solid-state imaging element of the second embodiment of the present technology, a Cu electrode pad and an electrode via are formed to be displaced relative to each other, that is, to be distant from each other.

In the example of FIG. 10, a manufacturing apparatus 150 includes an electrode via forming unit 161, a trench creation unit 163, and a Cu electrode pad forming unit 164.

The electrode via forming unit 161 forms the electrode via. The trench creation unit 163 creates a trench portion for forming the Cu electrode pad.

The Cu electrode pad forming unit 164 forms the Cu electrode pad. Note that, in the case of the example of FIG. 10, although not illustrated in FIG. 10, a semiconductor member forming unit may be included, and the semiconductor member forming unit forms a semiconductor device by bonding semiconductor members together.

<Operation Example of Manufacturing Apparatus>

Figure 11:
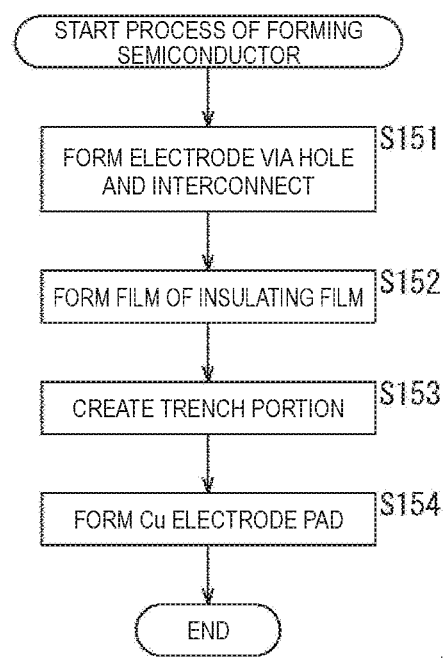
FIG. 11 is a flowchart illustrating a process of forming a semiconductor performed by the manufacturing apparatus of FIG. 10.

The following description describes, with reference to the flowchart of FIG. 11, a process of forming the semiconductor that is a solid-state imaging element of the second embodiment of the present technology. Note that the process of forming the semiconductor of FIG. 11 will be described by referring to the process diagrams of FIGS. 12A, 12B, 13A, and 13B where appropriate.

Figure 12A:
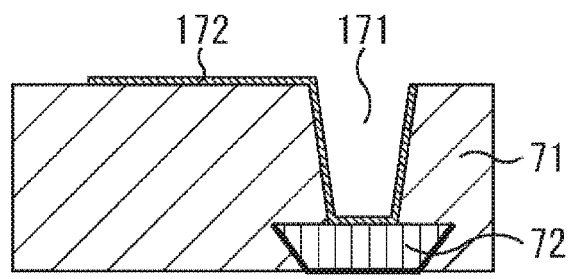
FIGS. 12A and 12B are process diagrams illustrating the process of forming a semiconductor of FIG. 11.
Figure 12B:
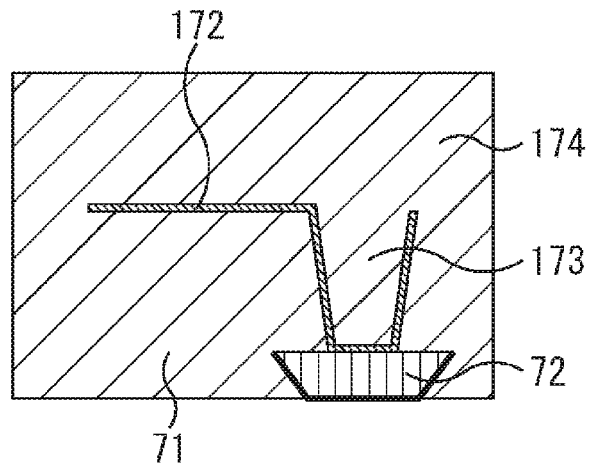

In step S151, as illustrated in FIG. 12A and FIG. 12B, the electrode via forming unit 161 forms an electrode via hole 171 and an electrically conductive interconnect 172 on an insulating film 71, which includes a Cu electrode via contact metal 72 formed therein. That is, the electrode via hole 171 and the electrically conductive interconnect 172 are formed by forming a Cu interconnect and thereafter performing, on the Cu interconnect, a lithography process, a dry etching process, and a sputtering process, in accordance with the BEOL process.

Here, a film for the electrically conductive interconnect 172 is formed along the side walls and the bottom of the electrode via hole 171 and the field by using an electrically conductive metal, such as tungsten (W), as a sputtering material. Note that, for an electrode via 173, an electrically conductive metal need not be completely embedded, and, it is sufficient that the film be formed in a manner to ensure an electrical connection between the electrode via contact metal 72 and the Cu electrode pad 76. With regard to the thickness of the side wall coverage film, it is desirable that the film be formed to a thickness of 100 nm or greater.

The width of the electrically conductive interconnect 172 is set in accordance with the size of the Cu electrode pad 76 so that a margin can be ensured, as in the first embodiment.

Next, in step S152, as illustrated in FIG. 12B, the electrode via forming unit 161 forms the film of an insulating film 174. During this, a portion of the insulating film 174 is filled into the electrode via hole 171, and thus the electrode via 173 is formed.

Figure 13A:
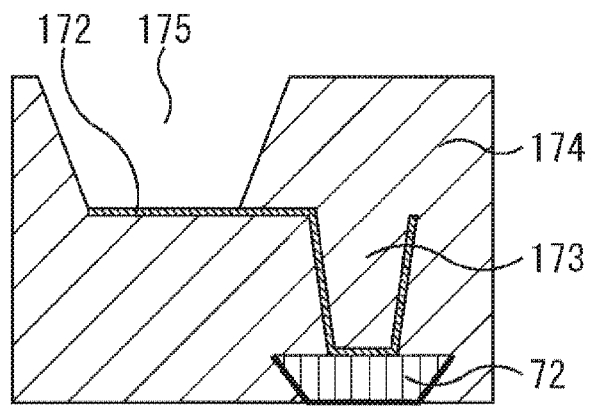
FIGS. 13A and 13B are process diagrams illustrating the process of forming a semiconductor of FIG. 11.

In step S153, as illustrated in FIG. 13A, the trench creation unit 163 creates, in a location away from the electrode via 173 and on the electrically conductive interconnect 172, a trench portion 175 for fabricating the Cu electrode pad 76.

Here, in the second embodiment, unlike in the first embodiment, no Cu material is used in the electrode via, and in addition, the volume of the metal film formed on the side walls is small compared with the Cu electrode via 73 of the first embodiment. As a result, Cu pumping does not occur. Consequently, there is no need to impose a significant limitation on the displacement width between the electrode via 173 and the Cu electrode pad 76.

In the case where the width of the opening of the electrode via 173 is narrow, however, sufficient filling of the insulating film may not be achieved, and therefore, it is desirable not to form a non-displaced Cu electrode member, that is, not to form the electrode pad 76 immediately over the electrode via 173. In the case where the portion immediately over the electrode via 173 is not completely covered with the insulating film 174, Cu plating flows into the electrode via 173 during formation of the Cu electrode pad 76. As a result, the shape of the Cu electrode pad 76 is unstable, and the bonding characteristics are degraded.

Figure 13B:
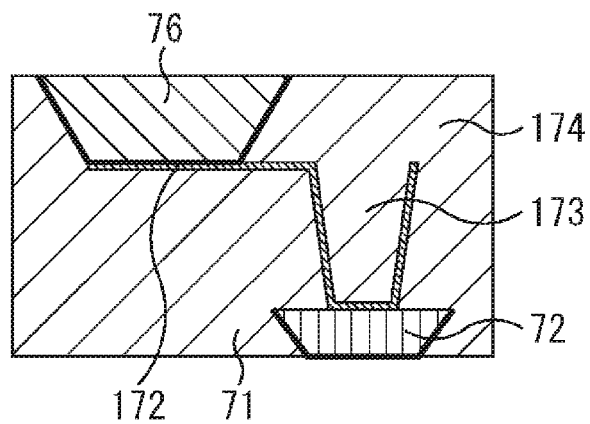

In step S154, as illustrated in FIG. 13B, the Cu electrode pad forming unit 164 fills the trench portion 175, which is for fabricating the Cu electrode pad 76, with Cu by performing a sputtering process and a Cu plating process and then performs a CMP process to form the Cu electrode pad 76, which is sufficiently highly planar to serve as a bonding surface.

In the second embodiment, compared with the first embodiment, the Cu volume of the Cu electrode is small, which, combined with the displacement structure, can doubly suppress the occurrence of Cu pumping. As a result, better bonding characteristics are achieved.

3. Third Embodiment

The third embodiment is an embodiment based on the premise that, to address issues such as a narrow width of the opening of the electrode via 173 as described above in the second embodiment, the state is such that embedding of the insulating film to the electrode via 173 can be sufficiently accomplished. Accordingly, the manufacturing apparatus for manufacturing a semiconductor device, which is a solid-state imaging element, of the third embodiment basically has a similar configuration to that of the manufacturing apparatus of the example of the second embodiment, and therefore descriptions thereof are omitted.

<Operation Example of Manufacturing Apparatus>

Furthermore, the process of forming the semiconductor that is a solid-state imaging element of the third embodiment of the present technology is substantially the same as the above-described example of the second embodiment and will therefore be described briefly with reference again to FIG. 11. Note that this process of forming a semiconductor will be described by referring to the process diagrams of FIGS. 14A 14B 15A, and 15B where appropriate.

Figure 14A:
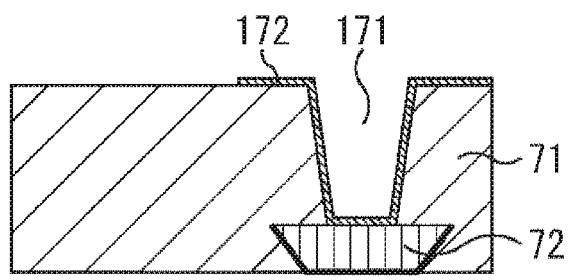
FIGS. 14A and 14B are process diagrams illustrating a process of forming a semiconductor, which is a solid-state imaging element, of a third embodiment of the present technology.
Figure 14B:
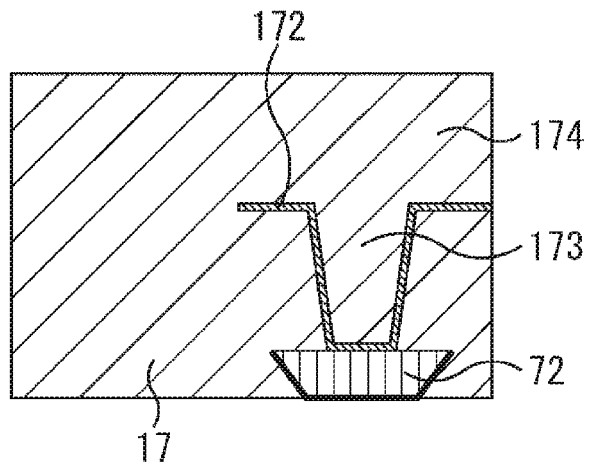

In step S151, as illustrated in FIG. 14A and FIG. 14B, the electrode via forming unit 161 forms an electrode via hole 171 and an electrically conductive interconnect 172 on an insulating film 71 over the Cu electrode via contact metal 72. Note that the electrically conductive interconnect 172 is formed to be connected to a Cu electrode pad 76, which is formed over the electrode via contact metal 72 (electrode via 173) (i.e., which is not distant from the electrode via 173), unlike the case of FIG. 12A and FIG. 12B.

Next, in step S152, as illustrated in FIG. 14B, the electrode via forming unit 161 forms the film of the insulating film 174. During this, a portion of the insulating film 174 is filled into the electrode via hole 171, and thus the electrode via 173 is formed.

Figure 15A:
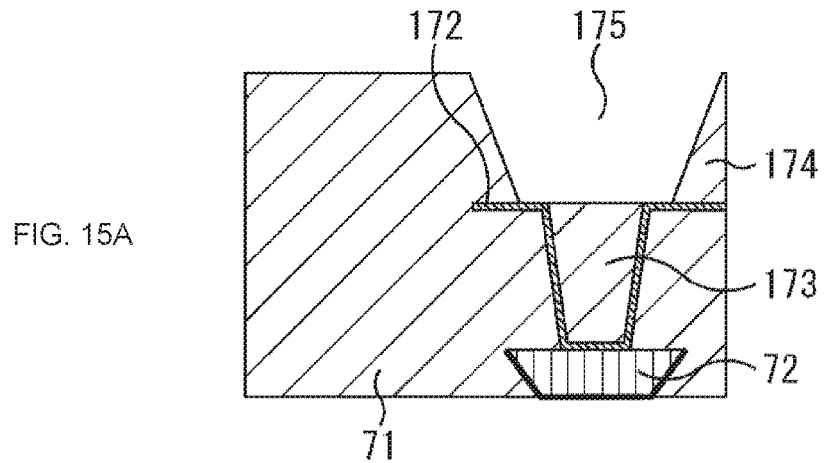
FIGS. 15A and 15B are process diagrams illustrating a process of forming a semiconductor, which is a solid-state imaging element, of a third embodiment of the present technology.

In step S153, as illustrated in FIG. 15A, the trench creation unit 163 creates, in a location over the electrode via 171 and on the electrically conductive interconnect 172, a trench portion 175 for fabricating the Cu electrode pad 76.

Figure 15B:
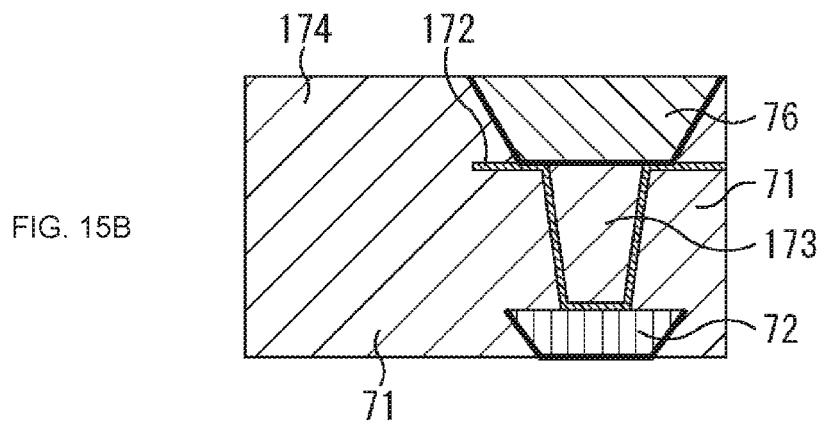

In step S154, as illustrated in FIG. 15B, the Cu electrode pad forming unit 164 fills the trench portion 175, which is for fabricating the Cu electrode pad 76, with Cu by performing a sputtering process and a Cu plating process and then performs a CMP process to form the Cu electrode pad 76, which is sufficiently highly planar to serve as a bonding surface.

In the case of the third embodiment, there is completely no need to impose a limitation on the displacement width between the electrode via 173 and the Cu electrode pad 76, and therefore, a flexible layout can be realized.

4. Fourth Embodiment

<Configuration Example of Manufacturing Apparatus>

Figure 16:
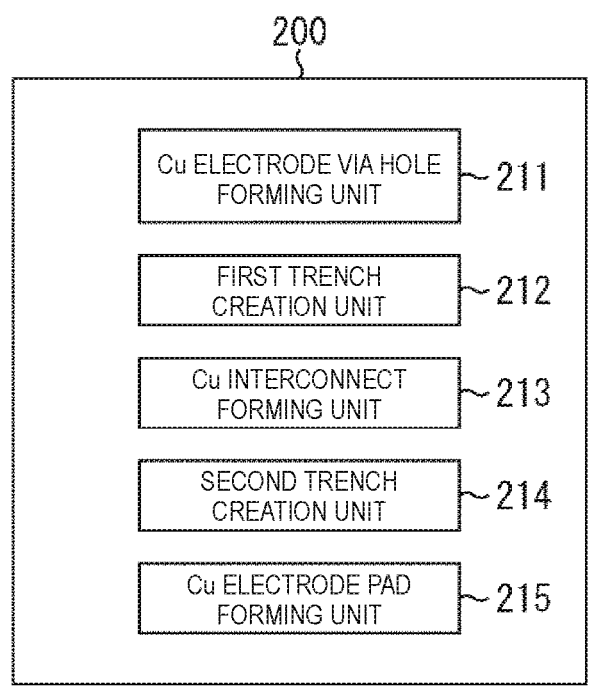
FIG. 16 is a block diagram illustrating a configuration example of a manufacturing apparatus for manufacturing a semiconductor device, which is a solid-state imaging element, of a fourth embodiment of the present technology.

FIG. 16 is a block diagram illustrating a configuration example of a manufacturing apparatus for manufacturing a semiconductor device, which is a solid-state imaging element, of the fourth embodiment of the present technology.

With the manufacturing apparatus of FIG. 16, too, in the fabrication of the Cu electrode used for bonding in the semiconductor device that is a solid-state imaging element of the fourth embodiment of the present technology, a Cu electrode pad and a Cu electrode via are formed to be displaced relative to each other, that is, to be distant from each other.

In the example of FIG. 16, a manufacturing apparatus 200 includes a Cu electrode via hole forming unit 211, a first trench creation unit 212, a Cu interconnect forming unit 213, a second trench creation unit 214, and a Cu electrode pad forming unit 215.

The Cu electrode via hole forming unit 211 forms a Cu electrode via hole. The first trench creation unit 212 creates a trench portion for a displaced Cu interconnect. The Cu interconnect forming unit 213 forms the Cu interconnect. The second trench creation unit 214 creates a trench portion for forming the Cu electrode pad. The Cu electrode pad forming unit 215 forms the Cu electrode pad.

Note that, in the case of the example of FIG. 16, too, although not illustrated in FIG. 16, a semiconductor member forming unit may be included, and the semiconductor member forming unit forms a semiconductor device by bonding semiconductor members together.

<Operation Example of Manufacturing Apparatus>

Figure 17:
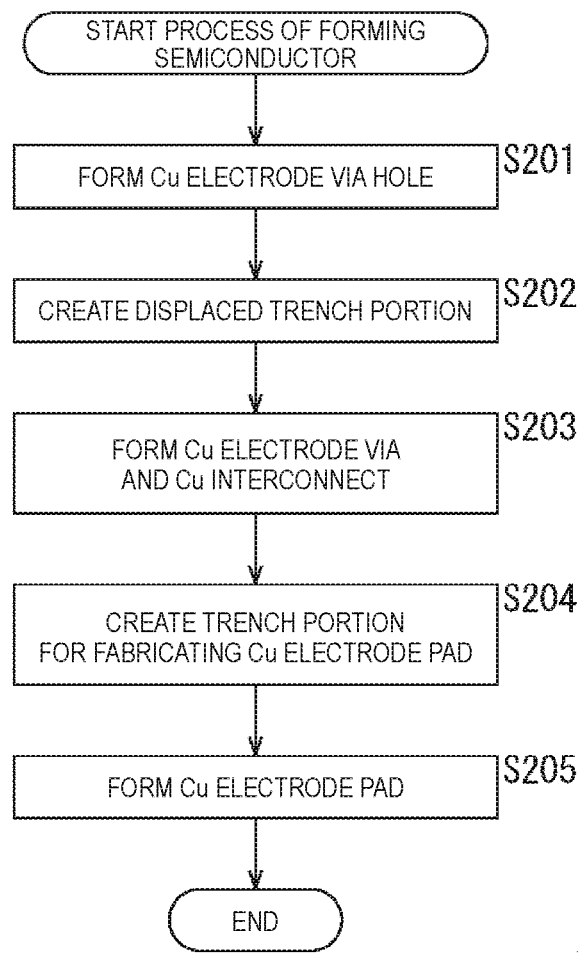
FIG. 17 is a flowchart illustrating a process of forming a semiconductor performed by the manufacturing apparatus of FIG. 16.

The following description describes, with reference to the flowchart of FIG. 17, a process of forming the semiconductor that is a solid-state imaging element of the fourth embodiment of the present technology. Note that the process of forming the semiconductor of FIG. 17 will be described by referring to the process diagrams of FIGS. 18A, 18B, 19A, 19B, and 19C where appropriate.

Figure 18A:
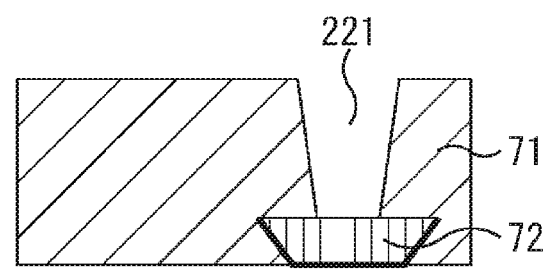
FIGS. 18A and 18B are process diagrams illustrating the process of forming a semiconductor of FIG. 17.

In step S201, as illustrated in FIG. 18A, the Cu electrode via hole forming unit 211 forms a Cu electrode via hole 221 in an insulating film 71 over a Cu electrode via contact metal 72. During that time, the Cu electrode via hole 221 is formed by forming a Cu interconnect and thereafter performing, on the Cu interconnect, a lithography process, a dry etching process, and a sputtering process, in accordance with the BEOL process.

Figure 18B:
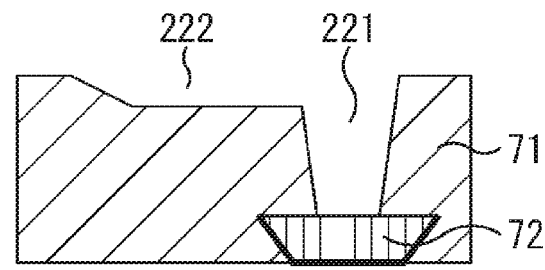

In step S202, as illustrated in FIG. 18B, the first trench creation unit 212 creates a displaced trench portion 222 by performing a lithography process and a dry etching process.

Figure 19A:
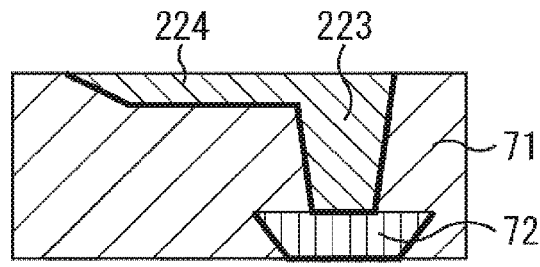
FIGS. 19A, 19B, and 19C are process diagrams illustrating the process of forming a semiconductor of FIG. 17.

In step S203, as illustrated in FIG. 19A, the Cu interconnect forming unit 213 fills the Cu electrode via hole 221 and the displaced trench portion 222 with Cu by performing a sputtering process and a Cu plating process, which is followed by a CMP process, thereby forming a Cu electrode via 223 and a displaced Cu interconnect 224.

Figure 19B:
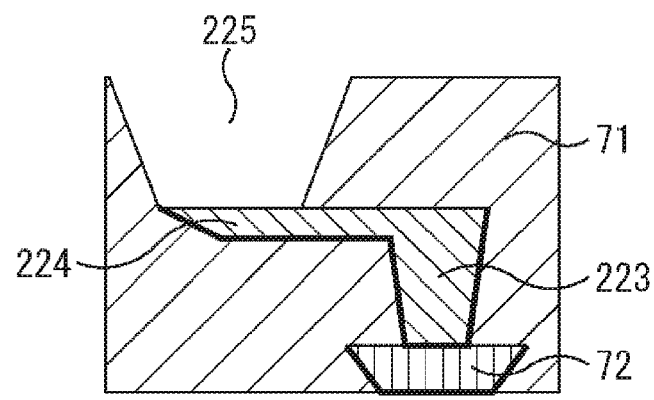
Figure 19C:
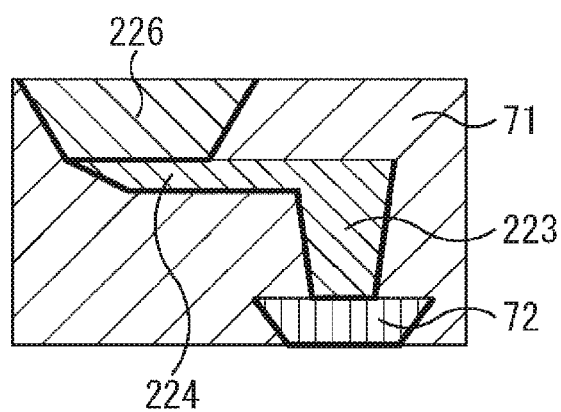

In step S204, as illustrated in FIG. 19B, the second trench creation unit 214 creates, in a location away from the Cu electrode via 223 and on the displaced Cu interconnect 224, a trench portion 225 for fabricating a Cu electrode pad.

In step S205, the Cu electrode pad forming unit 215 fills the trench portion 225, which is for fabricating the Cu electrode pad, with Cu by performing a sputtering process and a Cu plating process and then performs a CMP process to form a Cu electrode pad 226, which is sufficiently highly planar to serve as a bonding surface.

In the case of this example, the same Cu material is used for the Cu electrode via, the displaced Cu interconnect, and the Cu electrode pad to form the electrode; however, since the Cu electrode pad is not directly subjected to the influence of Cu volume thermal expansion stress from the Cu electrode via, the occurrence of Cu pumping can be suppressed, and therefore, good bonding characteristics and high reliability are achieved.

As described above, in a semiconductor device in which two or more semiconductor members are bonded and stacked together, the present technology makes it possible to suppress phenomena that can be caused as a result of the occurrence of Cu pumping due to volume thermal expansion stress of the Cu electrode via.

That is, semiconductor devices such as solid-state imaging elements have become, for example, multifunctional and accordingly, for example, a Cu electrode via is employed for the TSV, which results in an increase in the Cu volume of the Cu electrode via and therefore causes Cu volume thermal expansion stress in accordance with the coefficient of thermal expansion of Cu to be applied to the Cu electrode pad, with the result that Cu pumping occurs and bonding characteristics and reliability are degraded, and, to address this problem, the Cu electrode via and the Cu electrode pad are fabricated to be displaced relative to each other, so that the Cu electrode pad is not subjected to the influence of stress due to Cu volume thermal expansion of the Cu electrode via, thereby suppressing the occurrence of Cu pumping and preventing bonding characteristics and reliability from being degraded.

Furthermore, employing the structure in which the Cu electrode via and the Cu electrode pad are displaced relative to each other makes it possible to fabricate, with high yields, semiconductor devices such as solid-state imaging elements in which three or more semiconductor members are bonded and stacked together.

In addition, employing the structure in which the Cu electrode via and the Cu electrode pad are displaced relative to each other improves flexibility for the Cu electrode pad layout, with the adjustment of the amount of displacement.

That is, the limitation of disposing the Cu electrode pad immediately over the Cu electrode via is eliminated, which enables a flexible layout. Since an optimal Cu electrode pad layout in conformance with the pixel layout is made possible, pixel characteristics are improved, for example, reflection is suppressed and sensitivity variations are suppressed.

5. Usage Examples of Image Sensor

Figure 20:
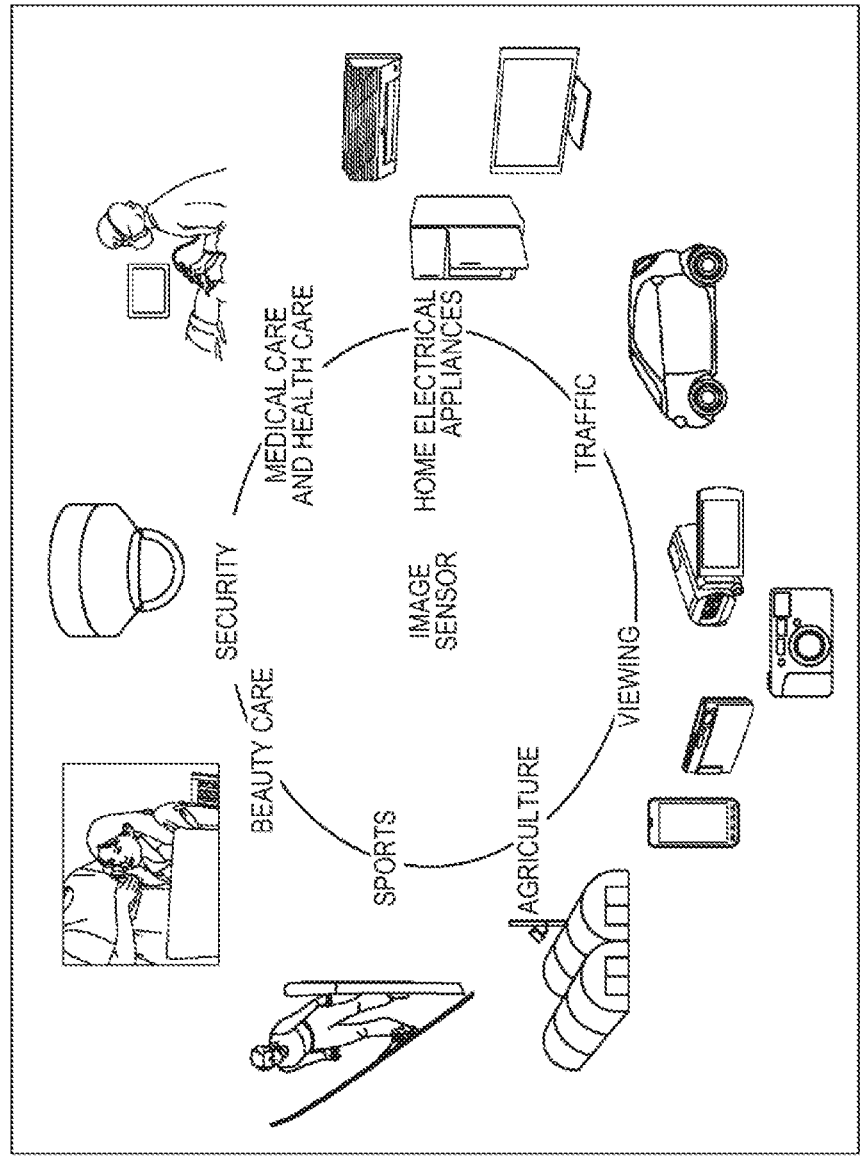
FIG. 20 is a diagram illustrating a usage example of an image sensor that employs the present technology.

FIG. 20 illustrates the usage examples of the above-described solid-state imaging sensor.

The above-described solid-state imaging sensor (image sensor) can be used for, for example, various cases in which light such as visible light, infrared light, ultraviolet light, or X-rays is detected as follows.

Devices that take images used for viewing, such as a digital camera and a portable appliance with a camera function.

Devices used for traffic, such as an in-vehicle sensor that takes images of the front and the back of a car, surroundings, the inside of the car, and the like, a monitoring camera that monitors travelling vehicles and roads, and a distance sensor that measures distances between vehicles and the like, which are used for safe driving (e.g., automatic stop), recognition of the condition of a driver, and the like.

Devices used for home electrical appliances, such as a TV, a refrigerator, and an air conditioner, to takes images of a gesture of a user and perform appliance operation in accordance with the gesture.

Devices used for medical care and health care, such as an endoscope and a device that performs angiography by reception of infrared light.

Devices used for security, such as a monitoring camera for crime prevention and a camera for personal authentication.

Devices used for beauty care, such as skin measurement equipment that takes images of the skin and a microscope that takes images of the scalp.

Devices used for sports, such as an action camera and a wearable camera for sports and the like.

Devices used for agriculture, such as a camera for monitoring the condition of the field and crops.

6. Example of Electronic Device

<Configuration Example of Electronic Device>

Further, the present technology is not limited to application to the solid state imaging device, but is also applicable to an imaging device. Here, the imaging device means a camera system such as a digital still camera and a digital video camera, and an electronic device that has an imaging function such as a mobile phone. Note that the imaging device is a modular form provided in an electronic device, that is, a camera module, in some cases.

Hence, a configuration example of an electronic device according to the present technology will be described, with reference to FIG. 21.

Figure 21:
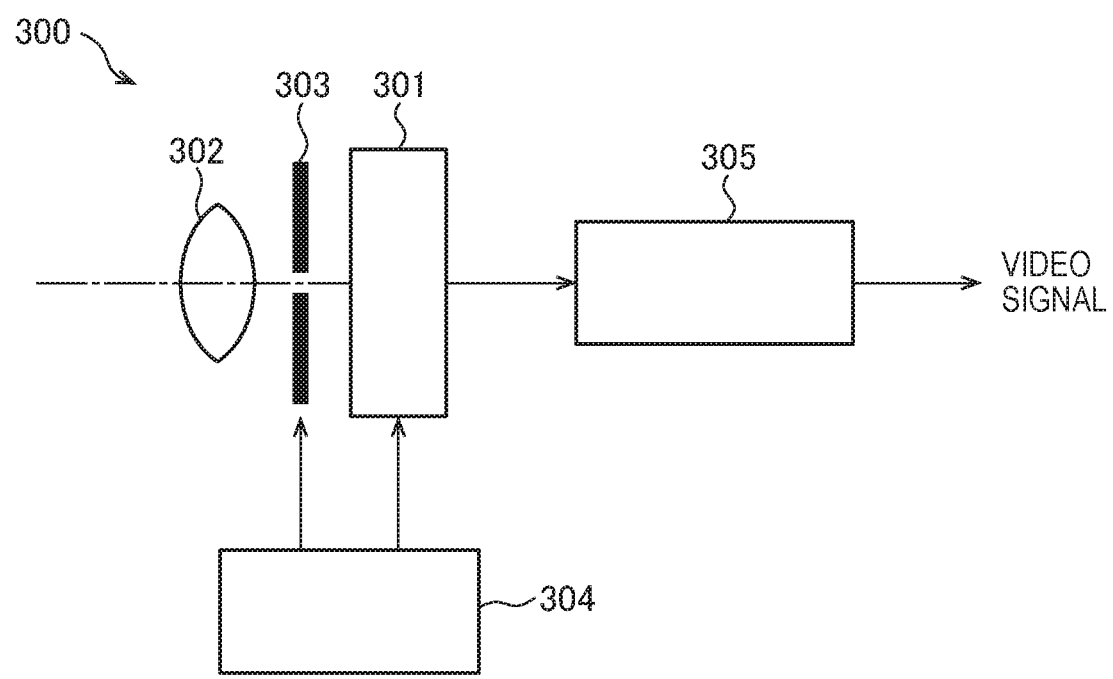
FIG. 21 is a block diagram illustrating a configuration example of an electronic device that employs the present technology.

An electronic device 300 illustrated in FIG. 21 includes a solid state imaging device (an element chip) 301, an optical lens 302, a shutter device 303, a drive circuit 304, and a signal processing circuit 305. The solid-state imaging device 1 illustrated in FIG. 1 described above is provided as the solid state imaging device 301.

The optical lens 302 causes an image light (incoming light) from an imaging subject to form an image on the imaging capturing surface of the solid state imaging device 301. Thereby, the signal electric charge is accumulated in the solid state imaging device 301 for a certain period. The shutter device 303 controls a light radiation period and a light blocking period to the solid state imaging device 301.

The drive circuit 304 supplies a driving signal for controlling the signal transfer operation of the solid state imaging device 301, the shutter operation of the shutter device 303, and the light emission operation of a light emission unit (not shown). The drive circuit 304 controls each operation using parameters set by a CPU (not shown). The solid state imaging device 301 transfers a signal, in accordance with the driving signal (timing signal) supplied from the drive circuit 304. The signal processing circuit 305 performs various types of signal processing to the signal output from the solid state imaging device 301. A video signal to which the signal processing is performed is stored in a storage medium such as a memory, and is output to a monitor.

7. Application Example to Endoscopic Surgery System

The present disclosure technology (this technology) can be applied to various products. For example, the present disclosure technology may be applied to the endoscopic surgery system.

Figure 22:
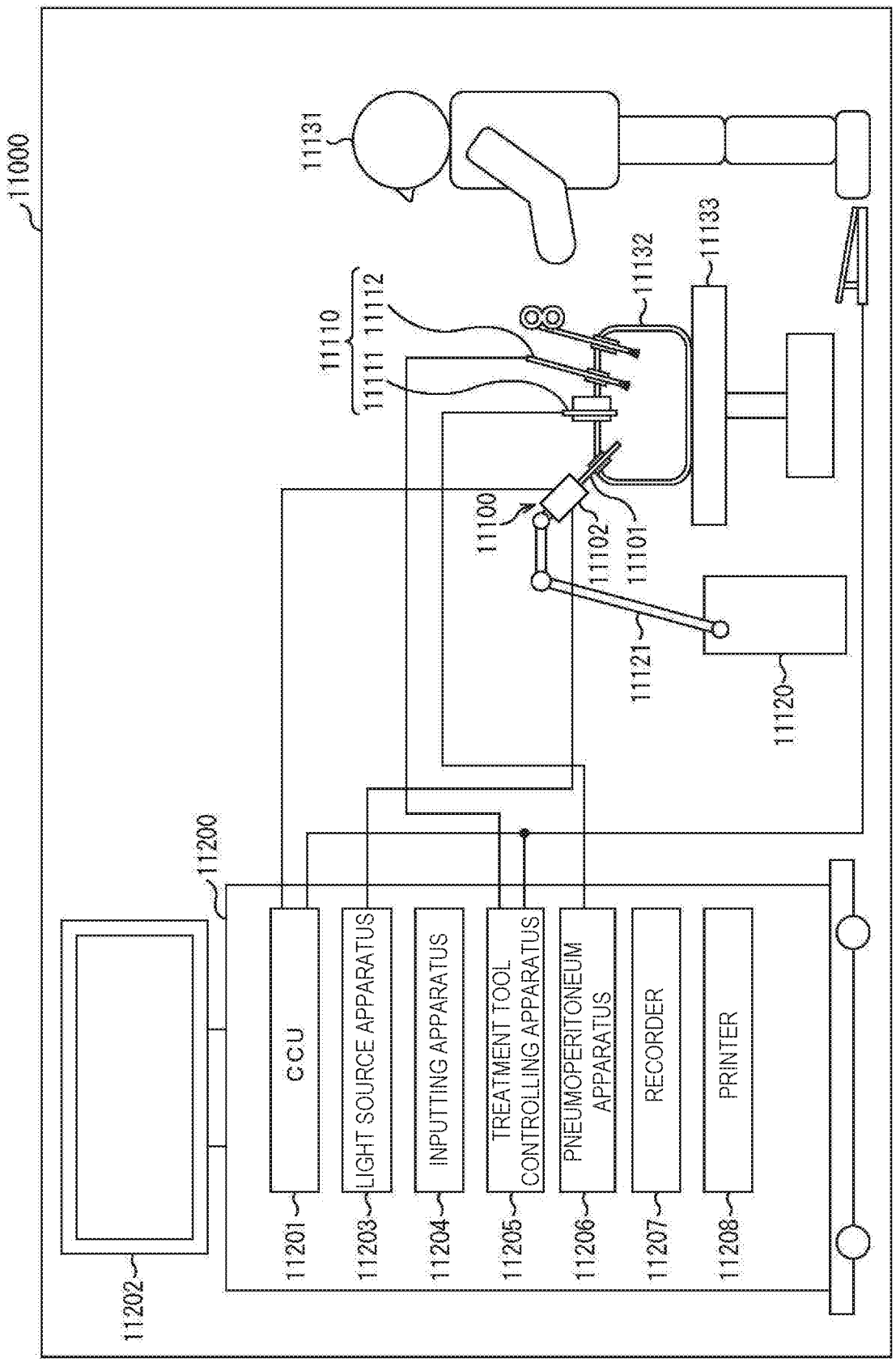
FIG. 22 is a view depicting an example of a schematic configuration of an endoscopic surgery system.

FIG. 22 is a view depicting an example of a schematic configuration of an endoscopic surgery system to which the technology according to an embodiment of the present disclosure (present technology) can be applied.

In FIG. 22, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 23:
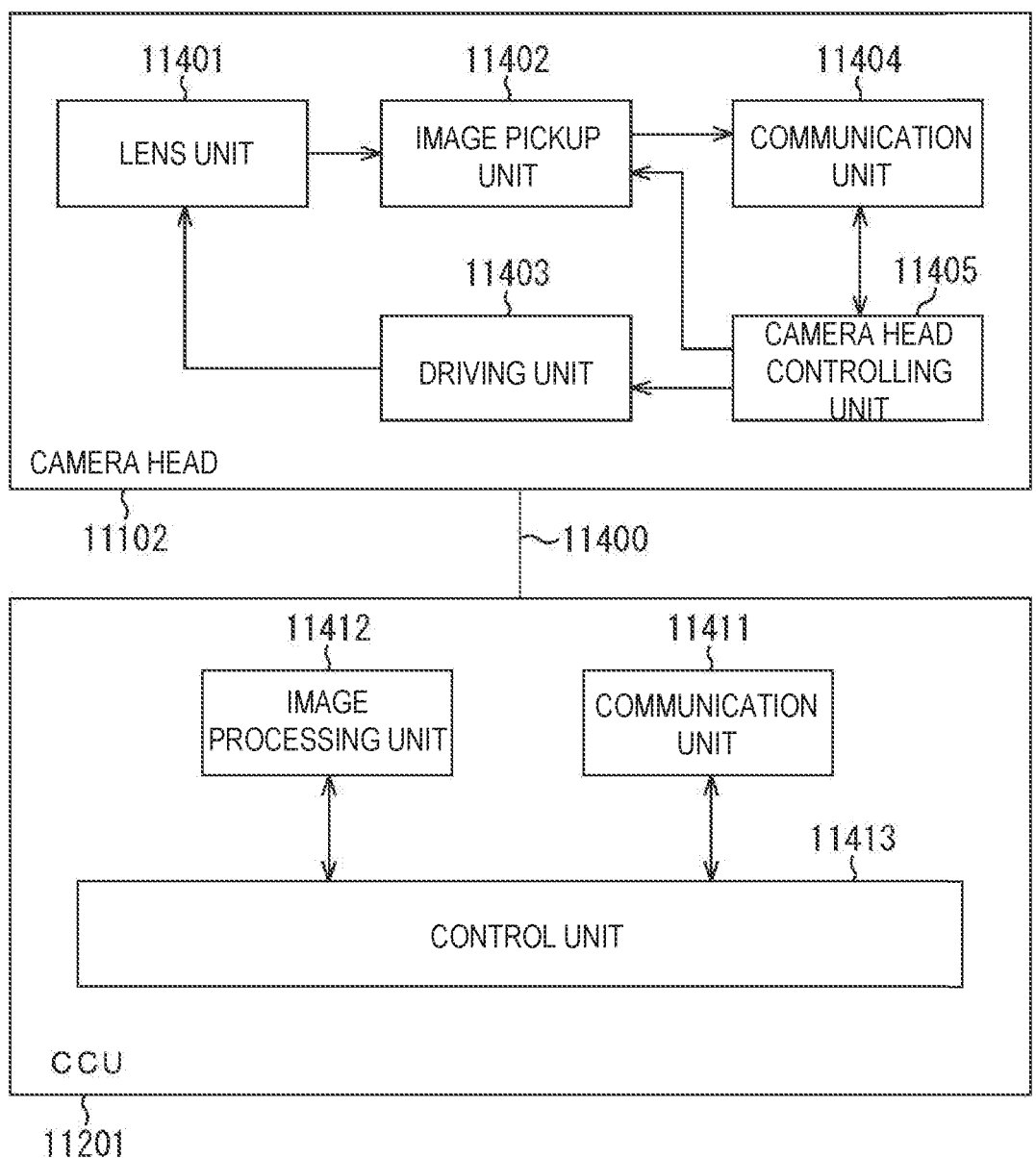
FIG. 23 is a block diagram depicting an example of a functional configuration of a camera head and a camera control unit (CCU).

FIG. 23 is a block diagram depicting an example of a functional configuration of the camera head 11102 and the CCU 11201 depicted in FIG. 22.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

The above description describes an example of an endoscopic surgery system to which the technology according to the present disclosure can be applied. For example, the technology according to the present disclosure can be applied to the endoscope 11100, the camera head 11102 (image pickup unit 11402 thereof), and the like, of the constituent elements described above. Specifically, the solid-state imaging device 1 of FIG. 1 can be applied to the image pickup unit 11402, for example. When the technology according to the present disclosure is applied to the image pickup unit 11402, clearer surgical site images can be obtained, and therefore, the operator can monitor the surgical site reliably.

Note that, here, an endoscopic surgery system is described as an example, but the technology according to the present disclosure may be applied to other systems such as a micrographic surgery system, for example.

8. Application Example to Mobile Body

A technology (the present technology) according to the present disclosure can be applied to various products. For example, the technology according to the present disclosure may also be realized as a device mounted in a mobile body of any type such as automobile, electric vehicle, hybrid electric vehicle, motorcycle, bicycle, personal mobility, airplane, drone, ship, or robot.

Figure 24:
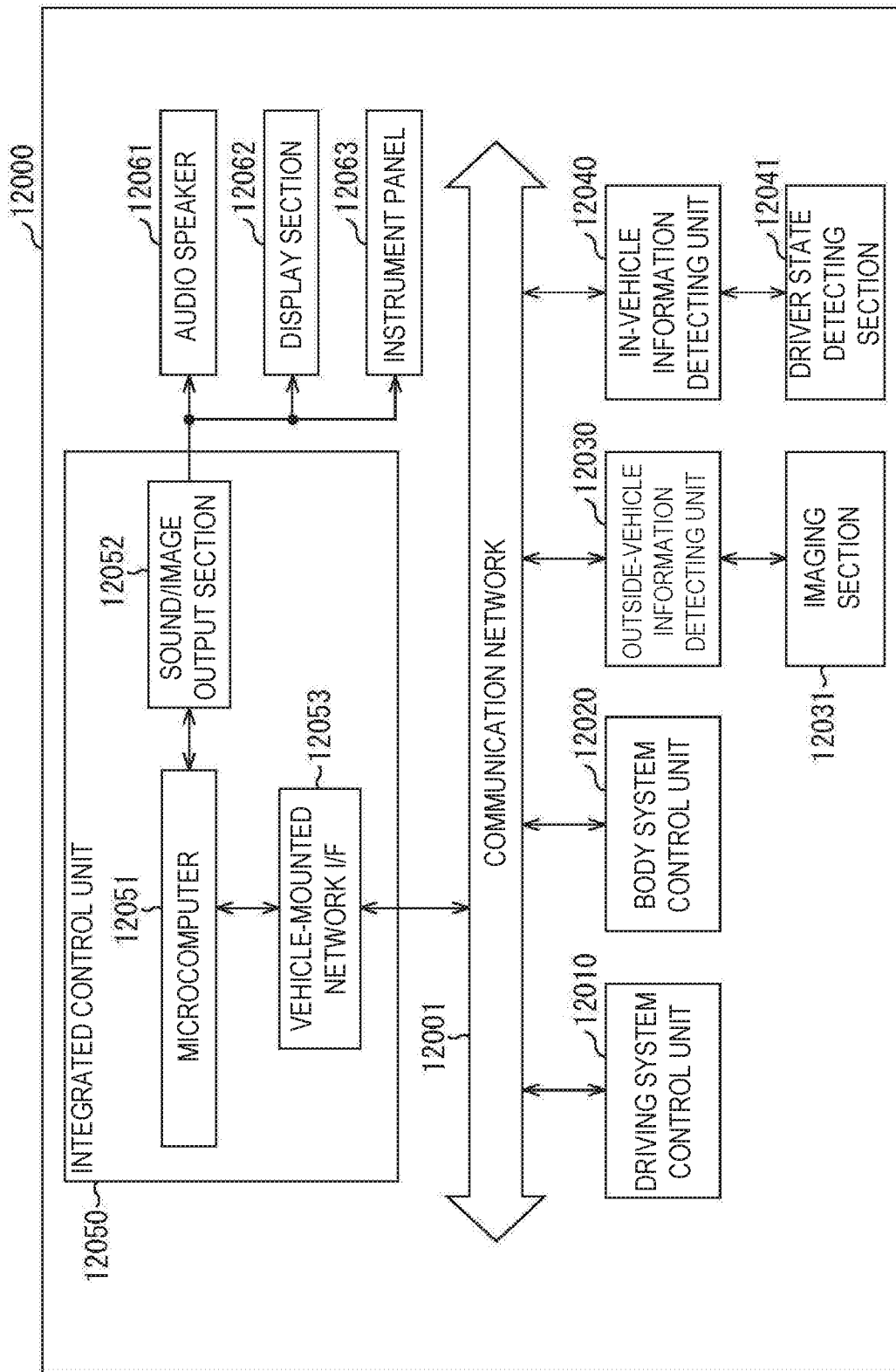
FIG. 24 is a block diagram depicting an example of schematic configuration of a vehicle control system.

FIG. 24 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 24, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 24, an audio speaker 12061, a display section 12062, and an instrument panel 12063 are illustrated as the output device. The display section 12062 may, for example, include at least one of an on-board display and a head-up display.

Figure 25:
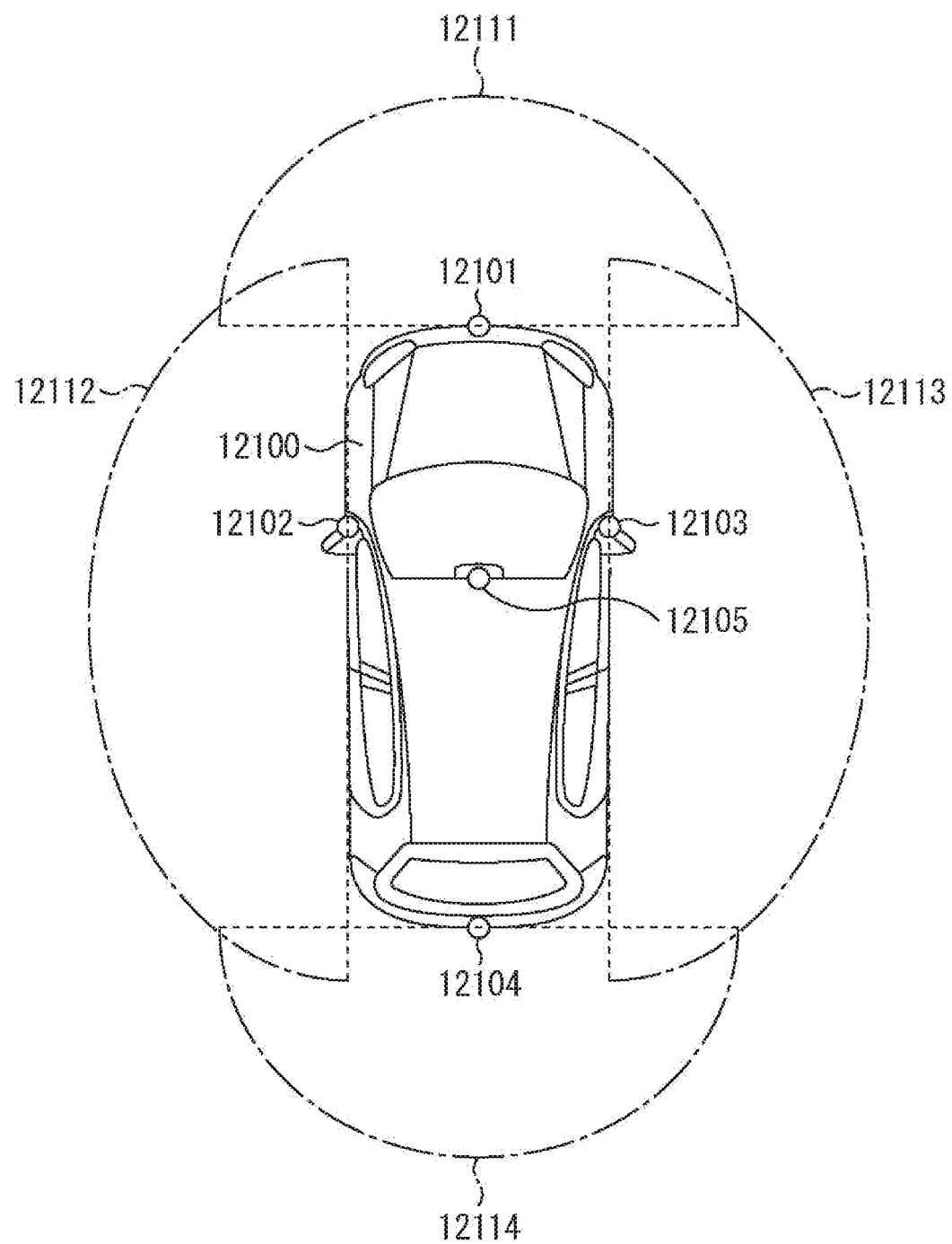
FIG. 25 is a diagram of assistance in explaining an example of installation positions of an outside-vehicle information detecting section and an imaging section.

FIG. 25 is a diagram depicting an example of the installation position of the imaging section 12031.

In FIG. 25, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 25 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

The above description describes an example of a vehicle control system to which the technology according to the present disclosure can be applied. The technology according to the present disclosure can be applied to the imaging section 12031 (including imaging sections 12101 to 12104) of the constituent elements described above. Specifically, the solid-state imaging device 1 of FIG. 1 can be applied to the imaging section 12031, for example. When the technology according to the present disclosure is applied to the imaging section 12031, special effects can be obtained. For example, clear images can be obtained in an in-vehicle device.

Note that, in this specification, steps in which a series of processes above described is written do not necessarily have to be performed in time series in line with the order of the steps, and instead may include processing that is performed in parallel or individually.

In addition, embodiments of the present disclosure are not limited to the above-described embodiments, and various alterations may occur insofar as they are within the scope of the present disclosure.

Further, an element described as a single device (or a processing unit) above may be divided and configured as a plurality of devices (or processing units). On the contrary, elements described as a plurality of devices (or processing units) above may be configured collectively as a single device (or a processing unit). Further, an element other than those described above may be added to each device (or a processing unit). Furthermore, a part of an element of a given device (or a processing unit) may be included in an element of another device (or another processing unit) as long as the configuration or operation of the system as a whole is substantially the same. In other words, an embodiment of the disclosure is not limited to the embodiments described above, and various changes and modifications may be made without departing from the scope of the disclosure.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Additionally, the present technology may also be configured as below.

(1)

A semiconductor device including:

a Cu electrode pad serving as a bonding surface for bonding a plurality of semiconductor members together; and an electrode via, the electrode via being a connection member that connects the Cu electrode pad to a lower-layer metal, in which the Cu electrode pad is formed in a location displaced from the electrode via.

(2)

The semiconductor device according to (1), in which the electrode via serves as a vertical signal line.

(3)

The semiconductor device according to (1) or (2), in which the electrode via includes Cu.

(4)

The semiconductor device according to (3), in which the Cu in the electrode via has a volume of $1.0E+10$ nm$^3$ or greater.

(5)

The semiconductor device according to (3), further including an electrically conductive metal that connects the electrode via to the Cu electrode pad, in which the electrically conductive metal is structured to cover a top of the electrode via.

(6)

The semiconductor device according to (5), in which the electrically conductive metal is aluminum or tungsten.

(7)

The semiconductor device according to (3), further including a Cu interconnect that connects the electrode via to the Cu electrode pad.

(8)

The semiconductor device according to (2), in which the electrode via is structured such that an electrically conductive metal other than Cu is formed on a side wall to be able to electrically connect at least the electrode via and the Cu electrode pad together and a space inside the side wall is filled with an insulating film.

(9)

The semiconductor device according to (8), in which the electrode via is structured such that the electrically conductive metal is formed to cover the side wall and the space inside the side wall is filled with the insulating film.

(10)

The semiconductor device according to any one of (1) to (9), in which, in accordance with volumes of the semiconductor members, the Cu electrode pad and the electrode via are provided in each of the semiconductor members to be bonded together.

(11)

The semiconductor device according to any one of (1) to (10), in which the Cu electrode pad and the electrode via are provided in one of the semiconductor members to be bonded together, and a Cu electrode is provided in another of the semiconductor members, the Cu electrode including the Cu electrode pad and a Cu electrode via formed immediately below the Cu electrode pad.

(12)

The semiconductor device according to any one of (1) to (11), in which the semiconductor device is a solid-state imaging device.

(13)

A manufacturing method including, by a manufacturing apparatus:

forming an electrode via, the electrode via being a connection member that connects a Cu electrode pad to a lower-layer metal, the Cu electrode pad serving as a bonding surface for bonding a plurality of semiconductor members together; and forming the Cu electrode pad in a location displaced from the electrode via.

(14)

An electronic device including:

a solid-state imaging device including a Cu electrode pad serving as a bonding surface for bonding a plurality of semiconductor members together, and an electrode via, the electrode via being a connection member that connects the Cu electrode pad to a lower-layer metal, the Cu electrode pad being formed in a location displaced from the electrode via;

a signal processing circuit configured to process an output signal output from the solid-state imaging device; and an optical system through which incident light passes to enter the solid-state imaging device.

REFERENCE SIGNS LIST 1 solid-state imaging device
50 manufacturing apparatus
61 Cu electrode via forming unit
62 electrically conductive interconnect forming unit
63 trench creation unit
64 Cu electrode pad forming unit
65 semiconductor member forming unit
71 insulating film
72 Cu electrode via contact metal
73 Cu electrode via
74 electrically conductive interconnect
75 trench portion
76 Cu electrode pad
81 displaced Cu electrode member
82 non-displaced Cu electrode member
83 bonding surface
91 Cu electrode via contact metal 92 Cu electrode via
93 Cu electrode pad
101 Si substrate
102 lens and color filter
103-1 to 103-3 structures
150 manufacturing apparatus
161 electrode via forming unit
163 trench creation unit
164 Cu electrode pad forming unit
171 electrode via hole
172 electrically conductive interconnect
173 electrode via
174 insulating film
175 trench portion
200 manufacturing apparatus
211 Cu electrode via hole forming unit
212 first trench creation unit
213 Cu interconnect forming unit
214 second trench creation unit
215 Cu electrode pad forming unit
221 Cu electrode via hole
222 displaced trench portion
223 Cu electrode via
224 displaced Cu interconnect
225 trench portion for fabricating Cu electrode pad
226 Cu electrode pad
300 electronic device
301 solid-state imaging device
302 optical lens
303 shutter device
304 drive circuit
305 signal processing circuit

The invention claimed is:

1. A semiconductor device, comprising:
a first Cu electrode pad configured to bond a first semiconductor member of a plurality of semiconductor members to a second semiconductor member of the plurality of semiconductor members;
a lower-layer metal; and
an electrode via configured to connect the first Cu electrode pad to the lower-layer metal, wherein
the first Cu electrode pad is in a location displaced from the electrode via,
an entirety of the first Cu electrode pad is in a non-overlapping arrangement with the electrode via,
the electrode via includes an electrically conductive metal, other than Cu, on each of a first side wall of the electrode via and a second side wall of the electrode via, and
a space between the electrically conductive metal on the first side wall and the electrically conductive metal on the second side wall includes an insulating film.

2. The semiconductor device according to claim 1, wherein the electrode via serves as a vertical signal line.

3. The semiconductor device according to claim 1, wherein the electrically conductive metal is configured to connect the electrode via to the first Cu electrode pad.

4. The semiconductor device according to claim 3, wherein the electrically conductive metal is one of aluminum or tungsten.

5. The semiconductor device according to claim 1, wherein
each semiconductor member of the plurality of semiconductor members includes the first Cu electrode pad and the electrode via based on a volume of each semiconductor member of the plurality of semiconductor members.

6. The semiconductor device according to claim 1, wherein
the first semiconductor member includes the first Cu electrode pad and the electrode via based on a volume of each of the plurality of semiconductor members,
the second semiconductor member includes a Cu electrode, and
the Cu electrode includes a second Cu electrode pad, and a Cu electrode via below the second Cu electrode pad.

7. The semiconductor device according to claim 1, wherein the semiconductor device is a solid-state imaging device.

8. A manufacturing method, comprising:
forming a lower-layer metal;
forming an electrode via on the lower-layer metal; and
forming a Cu electrode pad in a location displaced from the electrode via, wherein
the electrode via is configured to connect the Cu electrode pad to the lower-layer metal,
the Cu electrode pad is configured to bond a first semiconductor member of a plurality of semiconductor members to a second semiconductor member of the plurality of semiconductor members,
an entirety of the Cu electrode pad is in a non-overlapping arrangement with the electrode via,
the electrode via includes an electrically conductive metal, other than Cu, on each of a first side wall of the electrode via and a second side wall of the electrode via, and
a space between the electrically conductive metal on the first side wall and the electrically conductive metal on the second side wall includes an insulating film.

9. An electronic device, comprising:
an optical system configured to output light;
a solid-state imaging device configured to output an output signal based on the light output from the optical system, wherein
the output light is incident on the solid-state imaging device, and
the solid-state imaging device includes:
a Cu electrode pad configured to bond a first semiconductor member of a plurality of semiconductor members to a second semiconductor member of the plurality of semiconductor members;
a lower-layer metal; and
an electrode via configured to connect the Cu electrode pad to the lower-layer metal, wherein
the Cu electrode pad is in a location displaced from the electrode via,
an entirety of the Cu electrode pad is in a non-overlapping arrangement with the electrode via,
the electrode via includes an electrically conductive metal, other than Cu, on each of a first side wall of the electrode via and a second side wall of the electrode via, and
a space between the electrically conductive metal on the first side wall and the electrically conductive metal on the second side wall includes an insulating film; and
a signal processing circuit configured to process the output signal output from the solid-state imaging device.

* * * * *